US009403018B2

(12) United States Patent
McCabe et al.

(10) Patent No.: US 9,403,018 B2
(45) Date of Patent: *Aug. 2, 2016

(54) ACTIVITY SENSOR PROCESSING FOR PHRENIC NERVE ACTIVATION DETECTION

(71) Applicant: Cardiac Pacemakers, Inc., St. Paul, MN (US)

(72) Inventors: Aaron R. McCabe, Edina, MN (US); Holly E. Rockweiler, San Francisco, CA (US); Jacob I. Laughner, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/665,752

(22) Filed: Mar. 23, 2015

(65) Prior Publication Data

US 2015/0190643 A1 Jul. 9, 2015

Related U.S. Application Data

(63) Continuation of application No. 14/104,826, filed on Dec. 12, 2013, now Pat. No. 8,996,108, which is a continuation of application No. 12/787,563, filed on May 26, 2010, now Pat. No. 8,634,915.

(60) Provisional application No. 61/181,657, filed on May 27, 2009.

(51) Int. Cl.
*A61N 1/37* (2006.01)
*A61B 5/04* (2006.01)
(Continued)

(52) U.S. Cl.
CPC .......... *A61N 1/3702* (2013.01); *A61B 5/04001* (2013.01); *A61B 5/04004* (2013.01);
(Continued)

(58) Field of Classification Search
CPC ... A61N 1/36585; A61B 5/103; A61B 5/0205
See application file for complete search history.

(56) References Cited

U.S. PATENT DOCUMENTS 4,573,481 A 3/1986 Bullara et al.
5,658,318 A 8/1997 Stroetmann et al.
(Continued)

FOREIGN PATENT DOCUMENTS

EP 2435132 A1 4/2012
EP 2435132 B1 8/2013
(Continued)

OTHER PUBLICATIONS

Schuchert et al., "Two-year performance of a preshaped lead for left ventricular stimulation," Pacing Clinical Electrophysiology, vol. 27 (12), 2004, pp. 1610-1614.
(Continued)

*Primary Examiner* — Joseph Dietrich
(74) *Attorney, Agent, or Firm* — Schwegman Lundberg & Woessner, P.A.

(57) ABSTRACT

An implantable cardiac device includes a sensor for sensing patient activity and detecting phrenic nerve activation. A first filter channel attenuates first frequencies of the sensor signal to produce a first filtered output. A second filter channel attenuates second frequencies of the accelerometer signal to produce a second filtered output. Patient activity is evaluated using the first filtered output and phrenic nerve activation caused by cardiac pacing is detected using the second filtered output.

18 Claims, 21 Drawing Sheets

(51) Int. Cl.
   *A61B 5/08*    (2006.01)
   *A61B 5/103*   (2006.01)
   *A61N 1/365*   (2006.01)
   *A61B 5/00*    (2006.01)

(52) U.S. Cl.
   CPC .............. *A61B5/0809* (2013.01); *A61B 5/103* (2013.01); *A61N 1/36521* (2013.01); *A61N 1/36542* (2013.01); *A61N 1/36585* (2013.01); *A61B 5/686* (2013.01); *A61B 5/6869* (2013.01)

(56) References Cited

U.S. PATENT DOCUMENTS

| | | | |
|---|---|---|---|
| 6,076,015 | A  | 6/2000  | Hartley et al. |
| 6,221,011 | B1 | 4/2001  | Bardy |
| 6,270,457 | B1 | 8/2001  | Bardy |
| 6,277,072 | B1 | 8/2001  | Bardy |
| 6,280,380 | B1 | 8/2001  | Bardy |
| 6,312,378 | B1 | 11/2001 | Bardy |
| 6,336,903 | B1 | 1/2002  | Bardy |
| 6,358,203 | B2 | 3/2002  | Bardy |
| 6,368,284 | B1 | 4/2002  | Bardy |
| 6,398,728 | B1 | 6/2002  | Bardy |
| 6,415,183 | B1 | 7/2002  | Scheiner et al. |
| 6,440,066 | B1 | 8/2002  | Bardy |
| 6,772,008 | B2 | 8/2004  | Zhu et al. |
| 6,937,901 | B2 | 8/2005  | Zhu et al. |
| 7,299,093 | B2 | 11/2007 | Zhu et al. |
| 7,392,086 | B2 | 6/2008  | Sathaye |
| 8,200,331 | B2 | 6/2012  | Libbus et al. |
| 8,209,013 | B2 | 6/2012  | Brooke et al. |
| 8,265,736 | B2 | 9/2012  | Sathaye et al. |
| 8,626,292 | B2 | 1/2014  | McCabe et al. |
| 8,634,915 | B2 | 1/2014  | McCabe et al. |
| 9,149,642 | B2 | 10/2015 | McCabe et al. |
| 2002/0087199 | A1 | 7/2002  | Bange et al. |
| 2002/0161412 | A1 | 10/2002 | Sun et al. |
| 2003/0006536 | A1 | 1/2003  | Dunlap et al. |
| 2003/0065365 | A1 | 4/2003  | Zhu et al. |
| 2006/0241711 | A1 | 10/2006 | Sathaye |
| 2008/0071318 | A1 | 3/2008  | Brooke et al. |
| 2008/0234556 | A1 | 9/2008  | Brooke et al. |
| 2008/0294215 | A1 | 11/2008 | Sathaye |
| 2008/0300644 | A1 | 12/2008 | Sathaye |
| 2009/0043351 | A1 | 2/2009  | Sathaye et al. |
| 2010/0305638 | A1 | 12/2010 | McCabe et al. |

FOREIGN PATENT DOCUMENTS

| | | |
|---|---|---|
| JP | 2008518720 A     | 6/2008 |
| JP | 2009508594 A     | 3/2009 |
| WO | WO-2005076609 A1 | 8/2005 |
| WO | WO-2010138739 A1 | 12/2010 |

OTHER PUBLICATIONS

Stellbrink et al., "Technical considerations in implanting left ventricular pacing leads for cardiac resynchronization therapy", European Heart Journal Supp., vol. 6, 2004, pp. D43-D46.
All Non-Patent Literature Documents and Foreign Patent Documents Have Been Previously Uploaded in Parent U.S. Appl. No. 14/104,826, filed Dec. 12, 2003 and U.S. Appl. No. 12/787,563, filed May 26, 2010.
"U.S. Appl. No. 12/787,557,Advisory Action mailed Apr. 24, 2015",4 pgs.
"U.S. Appl.No. 12/787,557,Advisory Action mailed Jul. 31, 2013",3 pgs.
"U.S. Appl. No. 12/787,557, Examiner Interview Summary mailed Jul. 10, 2013", 3 pgs.
"U.S. Appl. No. 12/787,557, Final Office Action mailed Jan. 15, 2015", 9 pgs.
"U.S. Appl. No. 12/787,557 , Final Office Action mailed May 9, 2013", 8 pgs.
"U.S. Appl. No. 12/787,557, Non Final Office Action mailed Oct. 3, 2014", 8 pgs.
"U.S. Appl. No. 12/787,557, Non Final Office Action mailed Oct. 12, 2012", 8 pgs.
"U.S. Appl. No. 12/787,557, Notice of Allowance mailed May 28, 2015",7 pgs.
"U.S. Appl. No. 12/787,557, Response filed Jan. 11, 2013 to Non Final Office Action mailed Oct. 12, 2013", 9 pgs.
"U.S. Appl. No. 12/787,557, Response filed Mar. 13, 2015 to Final Office Action mailed Jan. 15, 2015", 10 pgs.
"U.S. Appl. No. 12/787,557, Response filed Apr. 14, 2015 to Final Office Action mailed Jan. 15, 2015", 10 pgs.
"U.S. Appl. No. 12/787,557,Response filed Jul. 9, 2013 to Final Office Action mailed May 9, 2013", 8 pgs.
"U.S. Appl. No. 12/787,557, Response filed Sep. 4, 2012 to Restriction Requirement mailed Aug. 3, 2012", 10 pgs.
"U.S. Appl. No. 12/787,557, Response filed Dec. 30, 2014 to Non Final Office Action mailed Oct. 3, 2014".
"U.S. Appl. No. 12/787,557, Restriction Requirementmailed Jun. 26, 2012", 7 pgs.
"U.S. Appl. No. 12/787,557, Restriction Requirementmailed Aug. 3, 2012", 9 pgs.
"U.S. Appl. No. 12/787,558, Applicant's Summary of Examiner Interview filed Sep. 6, 2013", 1 pg.
"U.S. Appl. No. 12/787,558, Final Office Action mailed Jun. 28, 2013", 8 pgs.
"U.S. Appl. No. 12/787,558, Non Final Office Action mailed Aug. 3, 2012", 7 pgs.
"U.S. Appl. No. 12/787,558, Notice of Allowance mailed Sep. 6, 2013",9 pgs.
"U.S. Appl. No. 12/787,558, Response filed Apr. 2, 2012 to Restriction Requirement mailed Mar. 1, 2012", 7 pgs.
"U.S. Appl. No. 12/787,558, Response filed Aug. 16, 2013 to Final Office Action mailed Jun. 28, 2013", 9 pgs.
"U.S. Appl. No. 12/787,558, Response filed Nov. 5, 2012 to Non Final Office Action mailed Aug. 3, 2012", 9 pgs.
"U.S. Appl. No. 12/787,558, Restriction Requirementmailed Mar. 1, 2012", 5 pgs.
"U.S. Appl. No. 12/787,563, Applicant's Summary of Examiner Interview filed Sep. 6, 2013", 1 pgs.
"U.S. Appl. No. 12/787,563, Final Office Action mailed Jun. 19, 2013", 6 pgs.
"U.S. Appl. No. 12/787,563, Non Final Office Action mailed Jun. 22, 2012", 6 pgs.
"U.S. Appl. No. 12/787,563, Non Final Office Action mailed Oct. 13, 2011", 6 pgs.
"U.S. Appl. No. 12/787,563, Notice of Allowance mailed Sep. 12, 2013", 10 pgs.
"U.S. Appl. No. 12/787,563, Response filed Feb. 13, 2012 to Non Final Office Action mailed Oct. 13, 2011", 10 pgs.
"U.S. Appl. No. 12/787,563, Response filed Aug. 16, 2013 to Final Office Action mailed Jun. 19, 2013", 13 pgs.
"U.S. Appl. No. 12/787,563, Response filed Aug. 28, 2012 to Non Final Office Action mailed Jun. 22, 2012", 10 pgs.
"U.S. Appl. No. 14/104,826, Examiner Interview Summary mailed May 22, 2014", 3 pgs.
"U.S. Appl. No. 14/104,826, Final Office Action mailed Sep. 25, 2014", 5 pgs.
"U.S. Appl. No. 14/104,826, Non Final Office Action mailed Mar. 14, 2014", 7 pgs.
"U.S. Appl. No. 14/104,826, Notice of Allowance mailed Nov. 25, 2014",6 pgs.
"U.S. Appl. No. 14/104,826, Response filed Jun. 6, 2014 to Non Final Office Action mailed Mar. 14, 2014", 11 pgs.
"U.S. Appl. No. 14/104,826, Response filed Nov. 7, 2014 to Final Office Action mailed Sep. 25, 2014", 6 pgs.
"European Application Serial No. 10721606.1, Decision to Grant mailed Jul. 25, 2013", 3 pgs.
"European Application Serial No. 10721606,1, Office Action mailed Jan. 11, 2012", 2 pgs.
"European Application Serial No. 10721606.1, Office Action mailed Mar. 11, 2013", 8 pgs.

(56) References Cited

OTHER PUBLICATIONS

"European Application Serial No. 12159736.3, Extended European Search Report mailed Oct. 9, 2013", 7 pgs.

"European Application Serial No. 12159736.3, Office Action mailed Nov. 11, 2013", 2 pgs.

"European Application Serial No. 12159736.3, Response filed May 2, 2014 to Extended European Search Report mailed Oct. 9, 2013", 28 pgs.

"European Application Serial No. 13172564.0, Extended European Search Report mailed Oct. 7, 2013", 6 pgs.

"European Application Serial No. 13172564.0, Office Action mailed Nov. 11, 2013", 2 pgs.

"European Application Serial No. 13172564.0, Response filed May 6, 2014 to Extended European Search Report mailed Oct. 7, 2013", 24 pgs.

"International Application Serial No. PCT/US2010/036434, International Preliminary Report on Patentability mailed Dec. 8, 2011", 11 pgs.

"International Application Serial No. PCT/US2010/036434, International Search Report mailed Oct. 1, 2010", 6 pgs.

"International Application Serial No. PCT/US2010/036434, Written Opinion mailed Oct. 1, 2010", 9 pgs.

"Japanese Application Serial No. 2011-282016, Office Action mailed Apr. 30, 2013", (w/ English Translation), 5 pgs.

"Japanese Application Serial No. 2011-282016, Response filed Jul. 29, 2013 to Office Action mailed Apr. 30, 2013", (w/ English Translation of Amended Claims), 7 pgs.

"Japanese Application Serial No. 2012-513261, Office Action mailed Apr. 16, 2013", (w/ English Translation), 7 pgs.

"Japanese Application Serial No. 2012-513261, Response filed Jul. 16, 2013 to Office Action mailed Apr. 16, 2013", (w/ English Translation of Amended Claims), 11 pgs.

ACTIVITY SENSOR PROCESSING FOR PHRENIC NERVE ACTIVATION DETECTION

RELATED APPLICATIONS

This application is a continuation of U.S. patent application Ser. No. 14/104,826, entitled "ACTIVITY SENSOR PROCESSING FOR PHRENIC NERVE ACTIVATION DETECTION", filed Dec. 12, 2013, now U.S. Pat. No. 8,996, 108, which is a continuation of U.S. patent application Ser. No. 12/787,563, entitled "ACTIVITY SENSOR PROCESSING FOR PHRENIC NERVE ACTIVATION DETECTION", filed May 26, 2010, now U.S. Pat. No. 8,634,915, which claims the benefit of Provisional Patent Application Ser. No. 61/181,657, filed on May 27, 2009, all of which are incorporated herein by reference.

FIELD OF THE INVENTION

The present invention relates generally to cardiac devices and methods, and, more particularly, to characterization of phrenic nerve activation and phrenic nerve activation avoidance during cardiac electrical therapy.

BACKGROUND OF THE INVENTION

When functioning normally, the heart produces rhythmic contractions and is capable of pumping blood throughout the body. The heart has specialized conduction pathways in both the atria and the ventricles that enable excitation impulses (i.e. depolarizations) initiated from the sino-atrial (SA) node to be rapidly conducted throughout the myocardium. These specialized conduction pathways conduct the depolarizations from the SA node to the atrial myocardium, to the atrio-ventricular node, and to the ventricular myocardium to produce a coordinated contraction of both atria and both ventricles.

The conduction pathways synchronize the contractions of the muscle fibers of each chamber as well as the contraction of each atrium or ventricle with the opposite atrium or ventricle. Without the synchronization afforded by the normally functioning specialized conduction pathways, the heart's pumping efficiency is greatly diminished. Patients who exhibit pathology of these conduction pathways can suffer compromised cardiac output.

Cardiac rhythm management (CRM) devices have been developed that provide pacing stimulation to one or more heart chambers in an attempt to improve the rhythm and coordination of atrial and/or ventricular contractions. CRM devices typically include circuitry to sense signals from the heart and a pulse generator for providing electrical stimulation to the heart. Leads extending into the patient's heart chamber and/or into veins of the heart are coupled to electrodes that sense the heart's electrical signals and deliver stimulation to the heart in accordance with various therapies for treating cardiac arrhythmias and dyssynchrony.

Pacemakers are CRM devices that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

A pace pulse must exceed a minimum energy value, or capture threshold, to "capture" the heart tissue, generating an evoked response that generates a propagating depolarization wave that results in a contraction of the heart chamber. If a pace pulse energy is too low, the pace pulses may not reliably produce a contractile response in the heart chamber and may result in ineffective pacing that does not improve cardiac function or cardiac output.

Pacing pulses can unintentionally stimulate nerves or muscles, even if the pulse energy is not sufficient to capture cardiac tissue. For example, a delivered pacing pulse may stimulate a patient's phrenic nerve, which runs proximate to the heart and innervates the diaphragm. The present invention provides methods and systems using phrenic nerve to detect phrenic nerve activation and avoid phrenic nerve activation during cardiac pacing therapy.

SUMMARY OF THE INVENTION

The present invention involves approaches for sensing phrenic nerve activation in conjunction with sensing patient activity and/or metabolic demand. Embodiments of the invention involve an implantable medical device that includes a pulse generator configured to deliver cardiac pacing to a heart. An accelerometer generates a signal modulated by acceleration that is available at an accelerometer output terminal. A first filter channel coupled to the accelerometer output terminal attenuates first frequencies of the accelerometer signal to produce a first filtered output. A second filter channel is coupled to the accelerometer output, separate from the first filter channel, attenuates second frequencies of the accelerometer signal to produce a second filtered output. Circuitry coupled to the first filter channel and the second filter channel evaluates a level of patient activity using the first filtered output and detects phrenic nerve activation caused by cardiac pacing using the second filtered output.

In some implementations, the first filter channel includes a high frequency cutoff of about 0.5 Hz to about 4 Hz. In some implementations, second filter channel comprises a low frequency cutoff of about 5 Hz. In some implementations, the second filter channel comprises an adaptable notch filter.

The second filter channel may have a filter characteristic that is adaptable based on cardiac rate and is configured to attenuate heart sounds from the second filtered output.

According to some aspects, a respiration sensor configured generate a signal modulated by respiration may also be used. In these implementations, the circuitry determines respiration phase and detects phrenic nerve activation based in part on respiration phase.

In some implementations, one or both of the first filter channel and the second filter channel comprises an analog filter. In some implementations, one or both of the first filter channel and the second filter channel comprises both analog and digital filters.

According to some aspects of the invention, analog circuitry is coupled between the accelerometer output terminal and the first and second filter channels. One or more of the first filter channel and the second filter channel includes a filter circuit that is substantially matched to an impulse response of the analog circuitry. For example, the filter circuit may substantially attenuate frequencies other than the impulse response frequencies of the analog circuitry. The filter circuitry can be individually mapped to the impulse response during device testing.

In some implementations, the circuitry includes a timer configured to time a phrenic nerve activation detection interval which is started upon or after delivery of a pacing pulse to a cardiac chamber and is stopped before delivery of a subsequent pacing pulse to the cardiac chamber.

Another embodiment of the invention is directed to a medical device adapted to deliver cardiac pacing. The device includes a sensor configured to produce a sensor signal at a sensor output terminal. Programmable signal processing circuitry is coupled to the sensor output terminal. The signal processing circuitry is programmable to have a first set of signal processing characteristics that produce a first output and to have a second set of signal processing characteristics that produces a second output. At least some of the first signal processing characteristics are different from at least some of the second signal processing characteristics. The device further includes processing circuitry configured to determine a rate-adaptation parameter using the first output and to detect phrenic nerve activation caused by the cardiac pacing using the second output.

According to some aspects, the filter circuitry includes an output terminal and is configured to produce the first filtered output at the output terminal during a first time period and to produce the second filtered output at the filter circuitry output terminal during a second time period.

According to some aspects, the filter circuitry comprises a first output terminal and a second output terminal and the filter circuitry is configured to produce the first filtered output at the first output terminal and the second filtered output at the second output terminal.

Another embodiment of the invention involves a method of operating an implantable medical device. Patient movement is sensed and a signal modulated by patient movement is generated at a sensor output terminal. The signal is filtered through separate filter channels to produce a first filtered output and a second filtered output. The separate filter channels include a first filter channel having first filter characteristics configured to attenuate a first set of frequencies from the signal and a second filter channel having second filter characteristics configured to attenuate a second set of frequencies from the signal. Patient activity is detected using the first filtered output. Phrenic nerve activation caused by cardiac pacing is detected using the second filtered output. An output is produced in response to detecting phrenic nerve activation.

The second filter characteristics may include an adaptable filter based on heart rate and configured to attenuate heart sounds from the signal.

According to some aspects of the invention, a transition zone is determined for phrenic nerve activation and a cardiac capture threshold is also determined. The pacing energy for cardiac pacing is set based on the phrenic nerve activation transition zone and the cardiac capture threshold.

According to some aspects of the invention, sensing for the phrenic nerve activation occurs during a phrenic nerve activation detection interval initiated after a cardiac pacing pulse is delivered to a cardiac chamber and terminated before a subsequent cardiac pacing pulse is delivered to the cardiac chamber.

Another embodiment of the invention is directed to an implantable medical device that delivers cardiac pacing to a heart. The device includes an impedance sensor configured to generate a signal modulated by patient respiration, the sensor signal available at a sensor output terminal. A first filter channel is coupled to the sensor output, the first filter channel configured to attenuate first frequencies of the sensor signal to produce a first filtered output. A second filter channel, separate from the first filter channel, is coupled to the sensor output, the second filter channel configured to attenuate second frequencies of the sensor signal to produce a second filtered output. Circuitry is configured to evaluate patient respiration using the first filtered output and to detect phrenic nerve activation caused by cardiac pacing using the second filtered output.

Yet another embodiment is directed to a cardiac rhythm management system for phrenic nerve activation characterization. The system includes an implantable cardiac pacing device having a plurality of electrodes implantable in a patient and having circuitry configured to output a plurality of cardiac pacing pulses through the electrodes and to modify one or more pacing parameters of the plurality of cardiac pacing pulses. A phrenic nerve activation sensor outputs a phrenic nerve activation signal indicative of activation of the patient's phrenic nerve. A respiration sensor outputs a respiration signal indicative of inhalation and exhalation respiratory activity of the patient. A controller configured to execute program instructions stored in memory to cause the system to identify a plurality of different respiratory phases based on the respiration signal for multiple respiratory cycles of the patient, deliver the plurality of cardiac pacing pulses within each of the identified plurality of different respiratory phases, and analyze the phrenic nerve stimulation signal to determine if one or more of the delivered plurality of pacing pulses activated the phrenic nerve of the patient based on the phrenic nerve activation signal.

A further embodiment involves an implantable medical device including a pulse generator configured to deliver cardiac pacing to a heart. An accelerometer generates a signal modulated by acceleration that is available at an accelerometer output terminal. A first filter channel is coupled to the accelerometer output terminal, the first filter channel attenuates first frequencies of the accelerometer signal to produce a first filtered output. A second filter channel is coupled to the accelerometer output, separate from the first filter channel, the second filter channel attenuates second frequencies of the accelerometer signal to produce a second filtered output. A respiration sensor outputs a respiration signal indicative of inhalation and exhalation respiratory activity of the patient. The medical device has circuitry coupled to the first filter channel, the second filter channel, and the respiration sensor. The circuitry is configured to evaluate a level of patient activity using the first filtered output and to detect phrenic nerve activation caused by cardiac pacing using the second filtered output. The circuitry identifies a plurality of different respiratory phases based on the respiration signal for multiple respiratory cycles of the patient, delivers cardiac pacing pulses within each of the identified plurality of different respiratory phases, and analyzes the second filtered output to determine if one or more of the delivered cardiac pacing pulses activates the phrenic nerve of the patient.

Yet a further embodiment is directed to an implantable medical device that includes a pulse generator configured to deliver cardiac pacing to a heart. An impedance sensor generates a signal modulated by patient respiration, the sensor signal available at a sensor output terminal. A first filter channel is coupled to the sensor output and attenuates first frequencies of the sensor signal to produce a first filtered output. A second filter channel, separate from the first filter channel, is coupled to the sensor output. The second filter channel attenuates second frequencies of the sensor signal to produce a second filtered output. Circuitry is used to evaluate patient respiration using the first filtered output and to detect phrenic nerve activation caused by cardiac pacing using the second filtered output. The circuitry identifies a plurality of different respiratory phases based on the first filtered output for multiple respiratory cycles of the patient, delivers cardiac pacing pulses within each of the identified plurality of different respiratory phases, and analyzes the second filtered output to determine if one or more of the cardiac pacing pulses activates the phrenic nerve of the patient.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
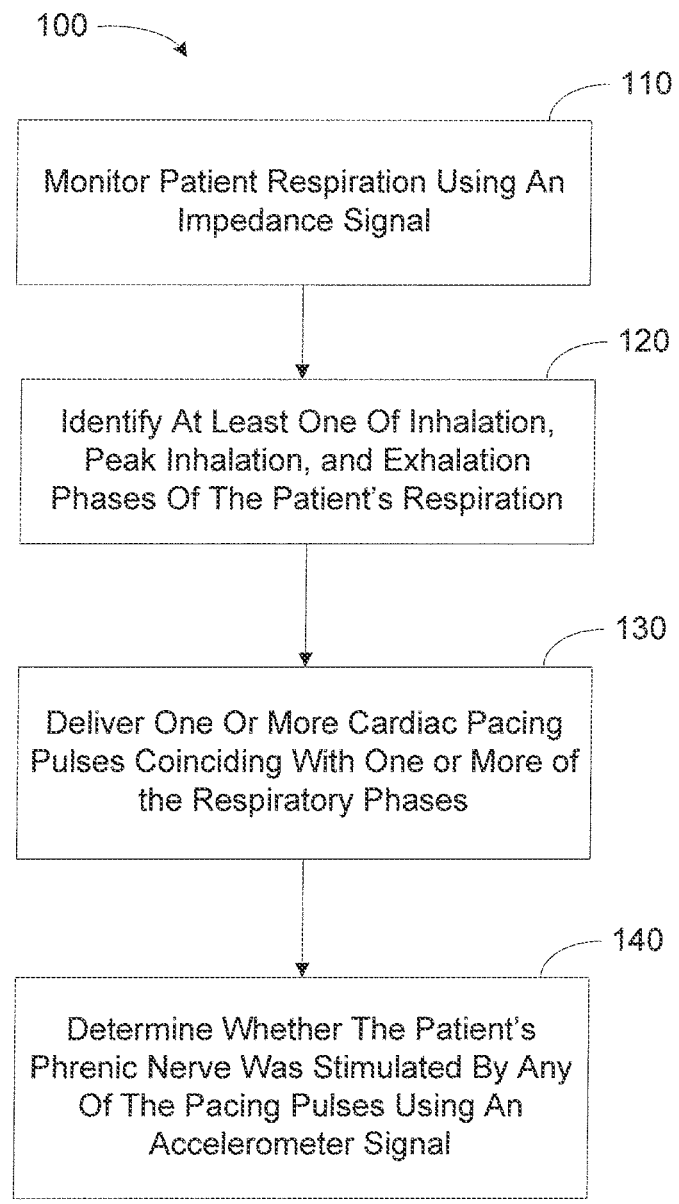
FIG. 1 is a flowchart illustrating a method of characterizing phrenic nerve activation relative to respiration in accordance with various embodiments of this disclosure.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Systems, devices, or methods according to the present invention may include one or more of the features, structures, methods, or combinations thereof described herein. For example, a device or system may be implemented to include one or more of the advantageous features and/or processes described below in various different embodiments. It is intended that such a device or system need not include all of the features described herein, but may be implemented to include selected features that provide for useful structures and/or functionality. Such a device or system may be implemented to provide a variety of therapeutic or diagnostic functions.

A wide variety of implantable cardiac monitoring and/or stimulation devices may be configured to implement phrenic nerve activation detection algorithms of the present invention. A non-limiting, representative list of such devices includes cardiac monitors, pacemakers, cardiovertors, defibrillators, resynchronizers, and other cardiac monitoring and therapy delivery devices. These devices may be configured with a variety of electrode arrangements, including transveneous, endocardial, and epicardial electrodes (i.e., intrathoracic electrodes), and/or subcutaneous, non-intrathoracic electrodes, including can, header, and indifferent electrodes, and subcutaneous array(s) or lead electrodes (i.e., non-intrathoracic electrodes).

In multi-electrode pacing systems, multiple pacing electrodes may be disposed in a single heart chamber, in multiple heart chambers, and/or elsewhere in a patient's body. Electrodes used for delivery of pacing pulses may include one or more cathode electrodes and one or more anode electrodes. Pacing pulses are delivered via the cathode/anode electrode combinations, where the term "electrode combination" denotes that at least one cathode electrode and at least one anode electrode are used. An electrode combination may involve more than two electrodes, such as when multiple electrodes that are electrically connected are used as the anode and/or multiple electrodes that are electrically connected are used as the cathode.

Typically, pacing energy is delivered to the heart tissue via the cathode electrode(s) at one or more pacing sites, with a return path provided via the anode electrode(s). If cardiac capture occurs, the energy injected at the cathode electrode site creates a propagating wavefront of depolarization which may combine with other depolarization wavefronts to trigger a contraction of the cardiac muscle. The cathode and anode electrode combination that delivers the pacing energy defines the pacing vector used for pacing.

Pacing pulses may be applied through multiple electrodes (i.e., pacing vectors defined by various electrode combinations) in a single cardiac chamber in a timed sequence during the cardiac cycle to improve contractility and enhance the pumping action of the heart chamber. It is generally desirable for each pacing pulse delivered via the multiple electrode combinations to capture the cardiac tissue proximate to the cathode electrode. Capture of cardiac tissue depends upon, among other things, the vector used to deliver the pulse and various pulse parameters, such as the amplitude and duration of the pulse.

A cardiac capture threshold can be determined using, among other methods, a step-down technique where a capture threshold is identified when loss of cardiac capture is detected after successive pacing cycles. A step-up technique can also be used, whereby a cardiac capture threshold is identified when cardiac capture is first detected after successive pacing cycles without cardiac capture. Cardiac capture can be detected using characteristics of an electrical cardiac signal indicating an intended cardiac response (e.g., a QRS complex).

Cardiac capture detection allows the cardiac rhythm management system to adjust the energy level of pace pulses to correspond to the optimum energy expenditure that reliably produces a contraction. Further, cardiac capture detection allows the cardiac rhythm management system to initiate a back-up pulse at a higher energy level whenever a pace pulse does not produce a contraction.

Stimulation characteristics of a cardiac pacing therapy are dependent on many factors, including the distance between the electrodes, proximity to targeted cardiac tissue, proximity to non-targeted tissue susceptible to unintended activation, type of tissue contacting and between the electrodes, impedance between the electrodes, resistance between the electrodes, and electrode type, among other factors. Such factors can influence the cardiac capture thresholds, as well as a patient's phrenic nerve activation thresholds. Stimulation characteristics can vary with physiologic changes, electrode migration, patient position, physical activity level, body fluid chemistry, hydration, and disease state, among other factors. Therefore, the stimulation characteristics for each electrode combination are unique and can change over time. As such, it can be useful to periodically determine the stimulation characteristics for each electrode combination for optimum pacing that avoids undesirable tissue activation.

Bi-ventricular pacing provides therapy options for patients suffering from heart failure. However, new challenges have been presented by placement of the left-ventricular lead via the coronary sinus in bi-ventricular pacing systems. Due to the proximity of the coronary veins to the phrenic nerve, left ventricular pacing may result in undesirable phrenic nerve stimulation. The phrenic nerve innervates the diaphragm, so unintended activation of the phrenic nerve can cause a patient to experience rapid contraction of the diaphragm, similar to a hiccup. Unintended activation of the phrenic nerve via a cardiac pacing pulse can be uncomfortable for the patient, and can interfere with breathing. Therefore, phrenic nerve activation from cardiac pacing may cause the patient to exhibit uncomfortable breathing patterns timed with the left-ventricular pace.

A phrenic nerve activation threshold for a pacing parameter (e.g., voltage, duration) for a particular electrode combination, above which the phrenic nerve will be activated by a pacing pulse, can be determined. One method for determining a phrenic nerve activation threshold includes sensing for some signature of phrenic nerve activation timed with the delivery of pacing pulses. If no change in phrenic nerve activation is sensed (e.g., is not lost or gained) using the level of electrical energy delivered, the energy level can be iteratively changed (e.g., decreased in a step down test or increased in a step up test) for subsequent trials of delivering electrical energy and monitoring for phrenic nerve activation until phrenic nerve activation is first lost (in the case of step-down scanning) or first detected (in the case of step-up scanning). The electrical energy level at which phrenic nerve activation is first detected or first lost can be the phrenic nerve activation threshold for the electrode combination tested. The energy delivered during such a scan could also be used to simultaneously perform other tests, such as searching for a cardiac capture threshold.

Methods for evaluating phrenic nerve activation that may be incorporated in embodiments of the present disclosure are disclosed in U.S. Pat. Nos. 6,772,008 and 7,392,086, each of which are herein incorporated by reference in their respective entireties.

Programming a pacing device to avoid undesirable stimulation, such as phrenic nerve activation, is not one dimensional, as many other factors can be important in setting appropriate pacing parameters. For example, a pace pulse must exceed a minimum energy value, or capture threshold, to produce an intended contraction of cardiac tissue. It is desirable for a pace pulse to have sufficient energy to stimulate capture of the heart without expending energy significantly in excess of the capture threshold. Thus, proper characterization of the various tissue activation thresholds provides efficient pace energy management. If the pace pulse energy is too low, the pace pulses may not reliably produce a contractile response in the heart and may result in ineffective pacing.

Another complication in determining appropriate pacing pulse parameters concerns seemingly erratic phrenic activation behavior even when pacing parameters are held constant. For example, in a step down test it is possible to lower cardiac pacing pulse voltage until phrenic nerve activation is not detected, and if the pacing parameters are held constant subsequent pacing parameters may not cause phrenic nerve activation. However, in some cases, the subsequent pacing pulses will cause phrenic nerve activation despite the same pacing parameters not causing phrenic nerve activation in one or more previous pulses.

The inventors have investigated this phenomenon and have linked the phases of respiration during which pacing pulses are delivered to increased and decreased susceptibility to phrenic nerve activation. For example, some subjects are more susceptible to phrenic nerve activation when the subjects are inhaling relative to other portions of the respiratory cycle, such as exhalation. Some subjects are more susceptible to phrenic nerve activation when they are at the deepest part of their breaths (at the point of maximum inhalation) relative to other portions of the respiratory cycle. Some subjects are less susceptible to phrenic nerve activation when the subject is exhaling or between breaths (e.g., not inhaling or exhaling) relative to other portions of the respiratory cycle. The particular susceptible phase for a particular patient may be influenced by the chosen pacing vector for pacing pulse delivery, or other pacing parameters, and could change chronically. The present disclosure concerns methods and systems for characterizing a patient's phrenic nerve activation response relative to respiration cycle and determining pacing parameters based on the characterization, among other things.

The cardiac pace pulse parameter range within which phrenic nerve activation is dependent on respiration phase is herein referred to as the transition zone. The transition zone corresponds to the pulse parameter range within which a cardiac pacing pulse will reliably (e.g., always) cause phrenic nerve activation above an upper boundary and will not cause phrenic nerve activation below a lower boundary, and between the upper and lower boundaries will sometimes cause phrenic nerve activation dependent on respiration cycle phase.

For example, if the cardiac pacing pulse parameter is voltage, then a transition zone can be the voltage range within which the respiratory phase influences whether a pulse having a voltage within the range causes phrenic nerve activation. Above the transition zone (e.g., voltages greater than the upper transition zone boundary), essentially all pulses will activate the phrenic nerve and below the transition zone (e.g., voltages less than the lower transition zone boundary) essentially no pulses will activate the phrenic nerve. Within the transition zone (e.g., voltage less than the upper transition zone boundary and greater than the lower transition zone boundary), any pulse having constant output parameters may or may not cause phrenic nerve activation, with phrenic nerve activation depending on the phase of the respiration cycle when the pulse was delivered. Different electrode combinations can have different thresholds and transitions zone ranges.

FIG. 1 illustrates a method 100 for characterizing a patient's phrenic nerve activation response relative to respiration. The method 100 includes monitoring 110 a patient's respiration using an impedance signal.

Figure 2:
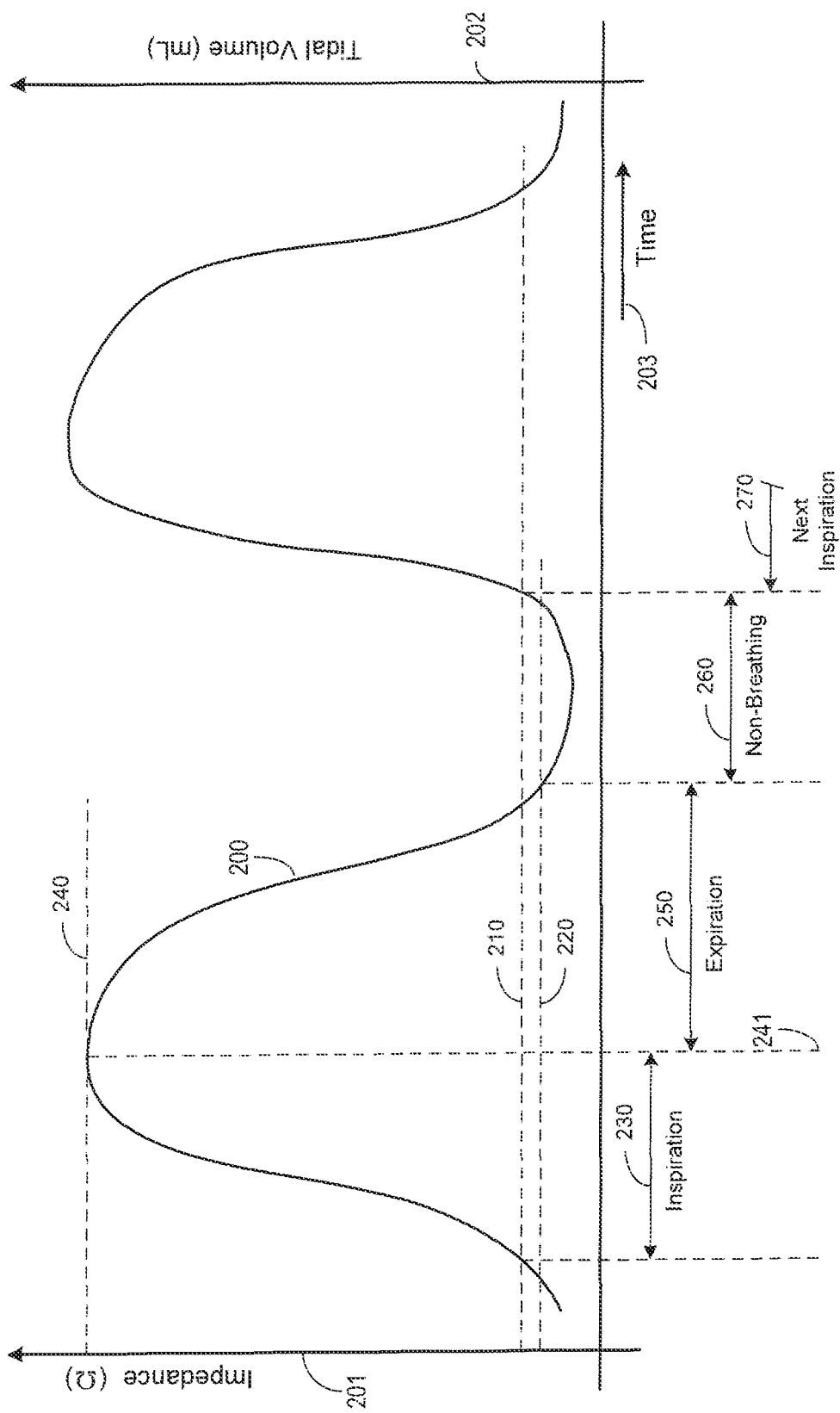
FIG. 2 is a graph illustrating respiration phases in accordance with embodiments of this disclosure.

FIG. 2 illustrates an impedance signal 200 that can be used in the method 100 of FIG. 1, as well in the other embodiments discussed herein. The impedance signal 200 is proportional to the transthoracic impedance illustrated as impedance 201 on the abscissa of the left side of the graph. The impedance 201 increases during any respiratory inspiration and decreases during any respiratory expiration. The impedance signal 200 is also proportional to the amount of air inhaled, denoted the tidal volume 202, illustrated on the abscissa of the right side of the graph.

The method 100 of FIG. 1 further includes identifying 120 at least one of inhalation, peak inhalation, and exhalation phases of the patient respiration based on the monitored 110 impedance signal. In some embodiments, all of these phases will be identified 120, and in some other embodiments only certain phases will be identified 120, such as inspiration and expiration.

A respiration cycle can be divided into an inspiration period corresponding to the patient inhaling, an expiration period corresponding to the patient exhaling, peak inhalation corresponding to the period after inhalation before exhalation, and a non-breathing period occurring after exhalation and before the next inhalation. Respiration phases can be established using an inspiration threshold 210 and an expiration threshold 220. The inspiration threshold 210 marks the beginning of an inspiration period 230 and is determined by the transthoracic impedance signal 200 rising above the inspiration threshold 210. The inspiration period 230 ends when the transthoracic impedance signal 200 is at maximum 240. The maximum transthoracic impedance signal 240 corresponds to both the end of the inspiration interval 230 and the beginning of an expiration interval 250. The expiration interval 250 continues until the transthoracic impedance 200 falls below an expiration threshold 220. A non-breathing interval 260 starts from the end of the expiration period 250 and continues until the beginning of a next inspiration period 270.

Taking the derivative of the impedance signal 200 can also identify respiratory phases. For example, the time 203 during which the derivative value of the impedance signal 200 is positive can correspond to the inspiration phase 230. The time 203 during which the derivative value of the impedance signal 200 is negative can correspond to the expiration phase 230. The time 203 during which the derivative value of the impedance signal 200 turns zero after being positive (inspiration) can correspond to the peak inspiration phase 241. A non-breathing phase 260 can be identified without use of a derivative as the time 203 during which the impedance signal 200 is below the expiration threshold 220.

The method 100 further includes delivering 130 one or more cardiac pacing pulses coinciding with one or more of the respiratory phases. For example, cardiac pacing pulses from a left ventricular lead electrode can be timed to be delivered within each of the respiration phases discussed herein, including during inspiration, peak inspiration, expiration, and non-breathing (peak expiration) phases.

The method 100 can then determine 140 whether the patient's phrenic nerve was stimulated by any of the pacing pulses using an accelerometer signal. Such a method can be used to determine if the cardiac pacing pulse parameters are associated with phrenic stimulation during one or more phases of respiration. Such techniques can also indicate if a patient is more susceptible to phrenic nerve activation during particular respiratory phases, by tracking during which phase or phases of respiration pulse delivery was correlated with phrenic nerve activation.

In method 100, as well as in the others discussed herein, it can be useful to hold cardiac pacing pulse parameters constant (e.g., constant voltage, duration, vector etc.) so that the timing of the pulses during the various respiration phases can be isolated as a variable. For example, pulses having particular voltage and duration parameters can be delivered during inspiration, peak inspiration, and expiration phases to determine whether respiratory phase plays a role in whether the phrenic nerve is stimulated using the parameter settings. One or more of the parameters can then be iteratively changed and tested to determine at which parameter settings the respiratory cycle influences phrenic nerve activation, and which cardiac pace pulse energy parameter settings are not associated with phrenic nerve activation during any phase of respiration.

A goal of various embodiments concerns finding cardiac pacing pulse parameter settings or ranges of settings that are not associated with phrenic nerve stimulation during any respiratory phase. Such settings can include pulse voltage, duration, and vector. Therefore, in various embodiments, different (and typically lower power) pacing pulse parameter settings are sought if any of the pulses delivered 130 during the various respiration phases were determined 140 to activate the patient's phrenic nerve. The method 100 can then be repeated until cardiac pacing pulse parameter settings are found that do not stimulate the patient's phrenic nerve during any of the respiratory phases.

The diaphragmatic response due to phrenic nerve stimulation can be detected using an accelerometer signal or other vibration detection methods. An accelerometer can measure accelerations of the sensor in one, two, or three dimensions. Accelerometers are sensitive sufficient to output a signal indicating the quick, hiccup-like chest movement experienced during phrenic nerve activation.

Figure 3:
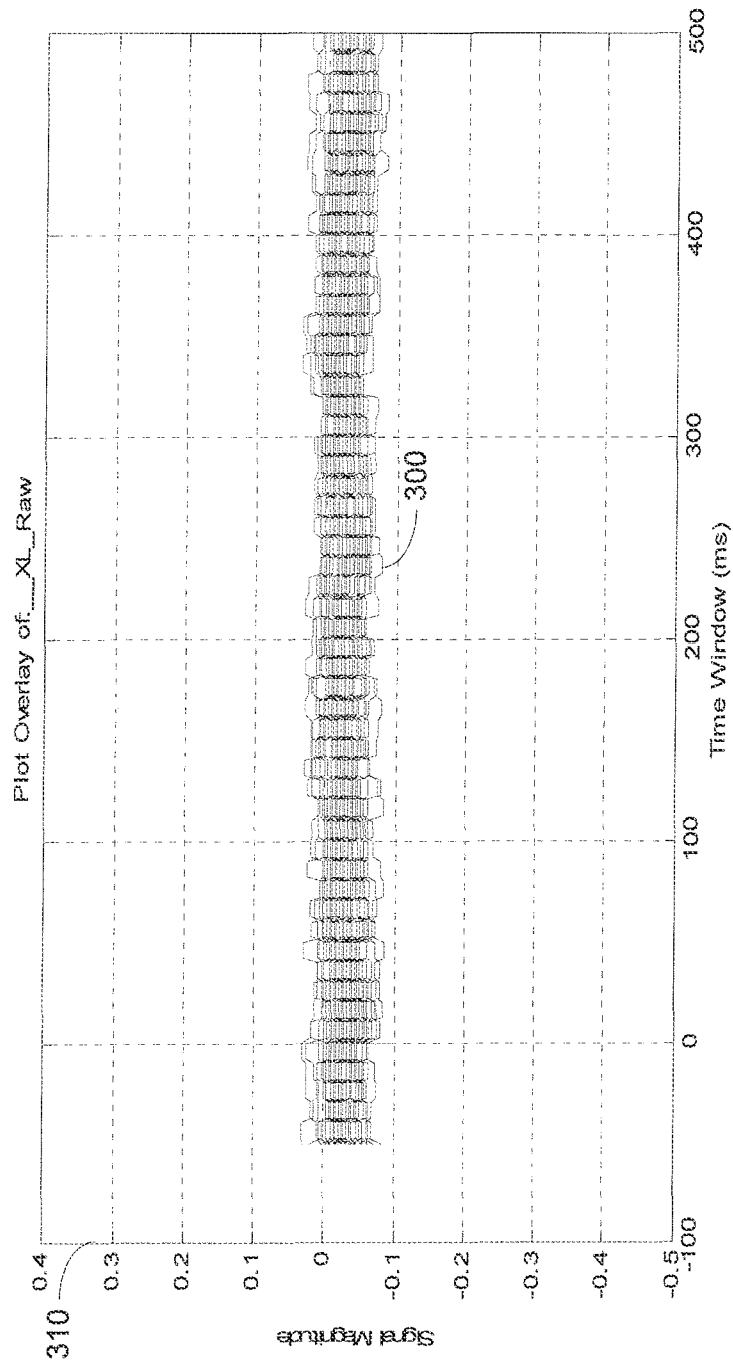
FIGS. 3-4 illustrate accelerometer data plots in accordance with embodiments of this disclosure.
Figure 4:
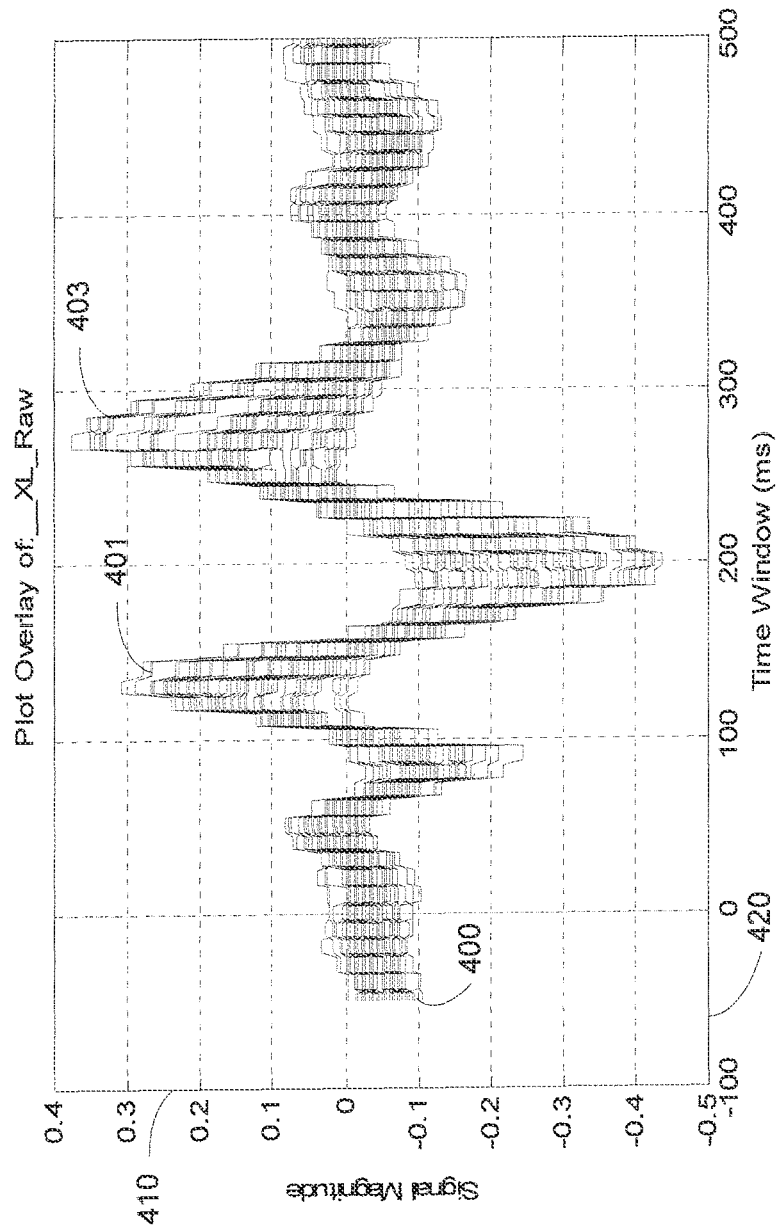

FIGS. 3-4 illustrate overlayed accelerometer signals (XL), measured in units of gravity 310. The accelerometer signals 300 of FIG. 3 are relatively flat and illustrate periods with no phrenic nerve activation via cardiac pacing pulse. As such, FIG. 3 shows very little deviation in the gravity signal 310 magnitude.

FIG. 4 shows accelerometer signals 400. Signals 400 have been overlayed to show a signature acceleration patterns of phrenic nerve activation as measured in gravity 410. In this example, acceleration associated with phrenic nerve activation is characterized by peaks 401 and 403.

Accelerometer signals could be evaluated in various ways to identify phrenic nerve activation. For example, a detection window can be initiated based on delivery 130 of a left ventricular pace pulse during a respiration phase of interest, the detection window focusing on accelerometer data. Such a window could open at the moment of pulse delivery or after a period of time after pulse delivery, such as a period of time that is slightly less than the estimated or tested amount of time for a pulse to cause diaphragmic motion perceivable by a sensor following delivery of the pulse. Other times to open a detection window are also contemplated. Such a detection window can have a length (measured in time, such as milliseconds) and satisfaction criteria (e.g., characteristics of the data indicative of phrenic nerve activation) that if met within the window indicate phrenic nerve activation by the cardiac pacing pulse. For example, if one or more peaks (e.g., peaks 401 and 403) are sensed within the window then phrenic nerve activation associated with the left ventricular pulse can be identified. Peaks and other features of accelerometer signals associated with phrenic nerve activation can be identified by timing, energy, and frequency-based methods or morphology analysis, for example. Limited duration of the window (e.g., a time between opening and closing of the window following pulse delivery) can focus collection of data associated with delivery of the cardiac pacing pulse for the amount of time needed to collect the necessary amount of data for phrenic nerve activation detection. In some embodiments, detection of phrenic nerve activation is not limited to windows, but particular techniques and/or heightened sensitivity for the detection of phrenic nerve activation are used within the windows. The opening of detection windows based on delivery of a left ventricular pace pulse to aid in detection of phrenic nerve activation associated with the left ventricular pace pulse can be performed in any embodiment discussed herein, including FIGS. 1-10.

Figure 5:
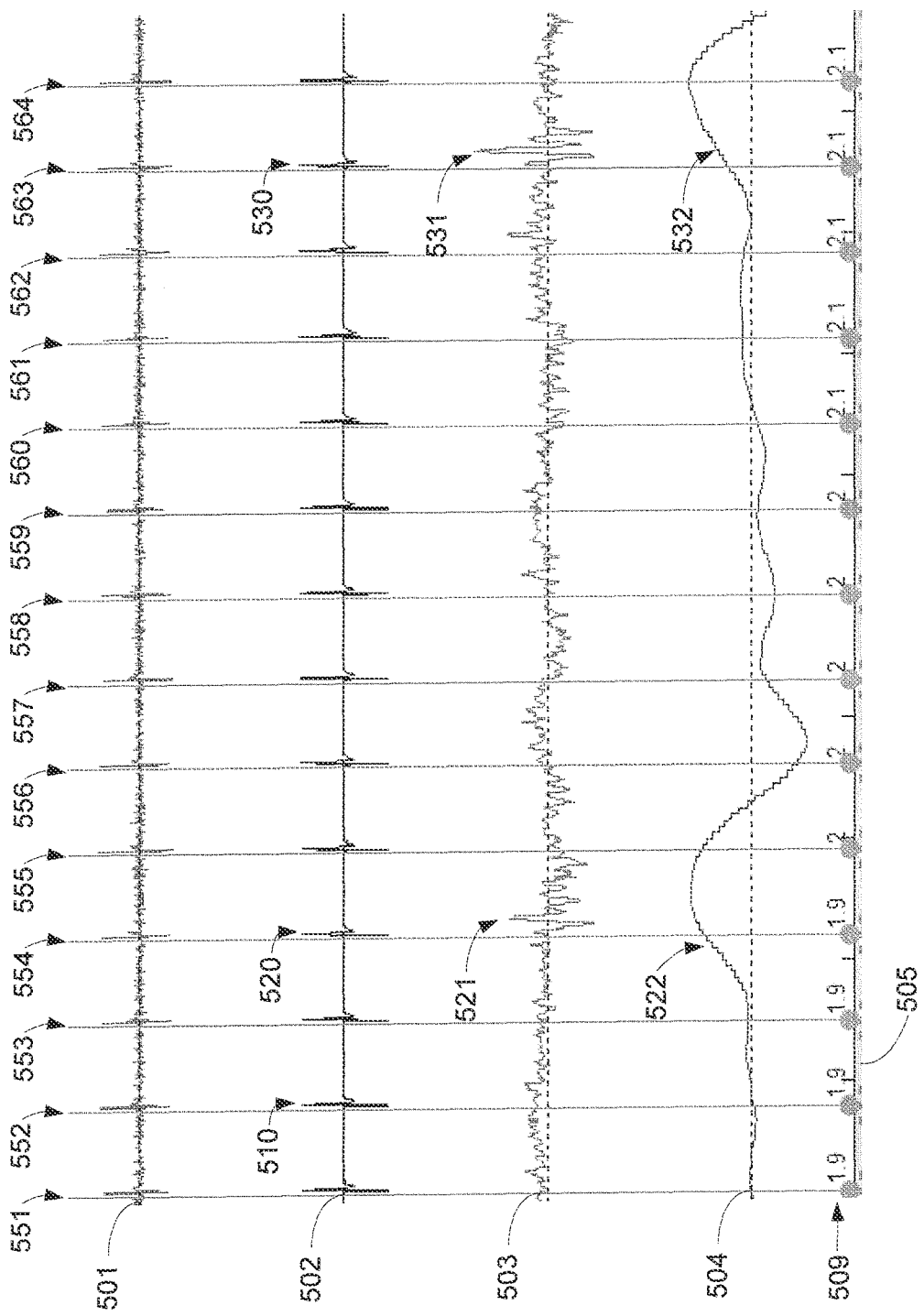
FIG. 5 is a multi-trace graph showing electrical cardiac, accelerometer, and impedance data collected during pulse delivery in accordance with embodiments of this disclosure.

FIG. 5 represents a time 505 alignment of right ventricular electrical cardiac signal 501, left ventricular electrical cardiac signal 502, accelerometer signal 503, and impendence signal 504. Cardiac pace pulses 551-564 are periodically delivered and associated cardiac activity (e.g., events 510, 520, 530) appears on the cardiac traces. The pulse voltage parameter 509 is increased between some of the pace pulses 551-564 from an initial 1.9 volts to 2.1 volts. Despite this continual pacing (increasing in voltage), continual phrenic nerve activation is not detected. Rather, the accelerometer signal 503 indicates that the occurrence of phrenic nerve activation is intermittent, and dependent on the respiratory phase in which the particular pulses 551-564 were delivered.

For example, the accelerometer signal 503 signatures 521 and 531 indicate that the phrenic nerve was stimulated by evidence of the characteristic phrenic nerve activation patterns discussed herein. These phrenic nerve activation accelerometer signal 503 signatures 521 and 531 immediately follow delivery of pulses 554 and 563 during inspiration phases 522 and 532 as indicated by the impedance signal 504. It is noted that for this particular subject, pulse 552 delivered during a non-breathing period, pulse 555 delivered during expiration, and pulse 564 delivered during peak inspiration, did not trigger phrenic nerve activation. As such, methods of the present disclosure indicate that this particular subject is particularly susceptible to phrenic nerve activation during inspiration periods relative to other respiration phases. Also, methods of the present disclosure indicate that this particular subject has a transition zone between at least 1.9 to 2.1 volts because phrenic nerve activation between these voltages is dependent on respiration phase.

Without wishing to be bound by any particular theory, one possible reason why phrenic nerve activation may be respiratory phase dependent for a subject is that the dimensions between the pacing electrodes and the phrenic nerve may change during the respiratory cycle, thereby changing the tissue through which the current flows. For example, as a particular patient inhales the current path between pacing electrodes may be more likely to traverse an area proximate the phrenic nerve, such that the patient is more susceptible to phrenic nerve activation during inhalation.

Figure 6:
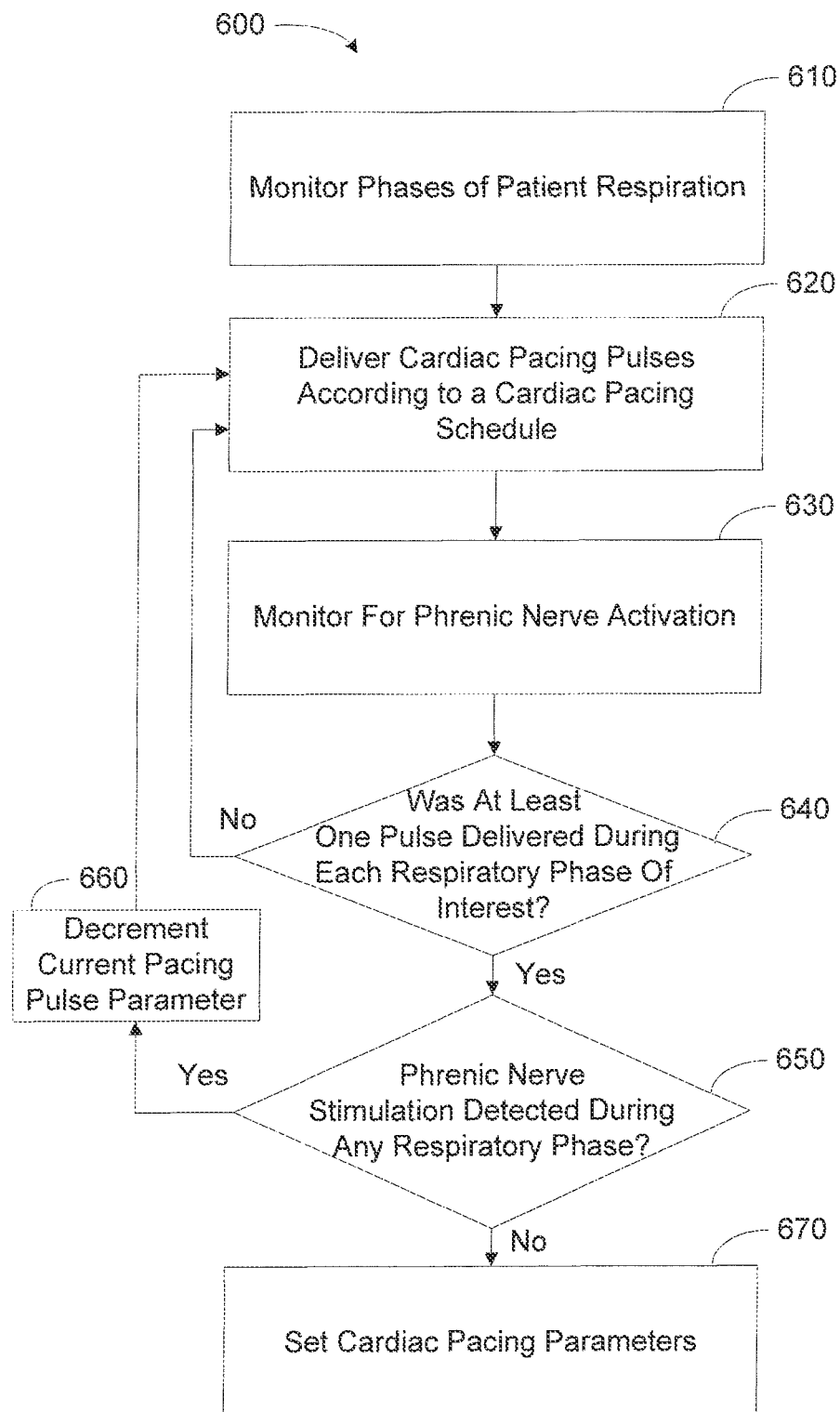
FIG. 6 is a flowchart illustrating a method of characterizing phrenic nerve activation in accordance with embodiments of this disclosure.

FIG. 6 illustrates a method 600 for finding cardiac therapy pulse parameter settings that avoid phrenic nerve activation. The method 600 can be initiated periodically on a preprogrammed schedule (e.g., once daily, weekly, or monthly, etc.), in response to detection of an event (e.g., sensing phrenic nerve activation, capture loss, and/or electrode combination reconfiguring), as part of an automatic ventricular threshold test, and/or by reception of a command (e.g., an input by a doctor or patient requesting automatic testing).

In some embodiments, one or more pacing parameters (e.g., pulse voltage, duration) will need to be set when the method 600 is initiated. The pacing parameter could be set at a previously used pacing value (e.g., when phrenic nerve activation was unexpectedly sensed), above a previously used value, a default value, or programmed by a physician. In the case of a step-up test, it can be preferable to have the pacing parameter initially set at a relatively low setting, below which it is thought that phrenic nerve activation is unlikely. In the case of a step-down test, it can be preferable to have the pacing parameter initially set at a relatively high setting at which it is thought phrenic nerve activation is likely. The method 600 is directed to a step-down test. However, the steps of the method 600 could be adapted and used in a step-up test.

The method 600 includes monitoring 610 phases of patient respiration. Monitoring 610 can be performed using various techniques that can identify respiratory phases, such as by collecting an impedance signal in the manner of FIG. 2. Cardiac pacing pulses can be delivered 620 according to a cardiac pacing schedule concurrent or interspaced with monitoring 610. During and/or after delivery 620 of each cardiac pacing pulse, phrenic nerve activation is monitored 630, such that activation of the phrenic nerve by any of the delivered 620 cardiac pacing pulses is identified. Monitoring 630 for phrenic nerve activation can be done by any technique for identifying phrenic nerve stimulation, such as by using an accelerometer in the manner of FIGS. 3-5. Phrenic nerve activation can also be sensed using an impedance sensor, which may show an abrupt disruption in the impedance signal breathing pattern if the phrenic nerve is activated (e.g., such as an abrupt disruption in the rhythmic breathing patterns of the impedance signal 200 in FIG. 2).

After delivery 620 of each pulse, or at other times (e.g., every minute, after delivery 620 of every 10 pulses, or after each respiratory phase or cycle), it is determined whether at least one pulse has been delivered during each respiratory phase of interest 640. It is noted that step 640, as well as the other techniques described herein, refer to pulse delivery in an occurrence of a phase of interest, not in each occurrence of each phase of interest. For example, if the respiratory phase of interest is inspiration, then 5 cycles of breathings will have 5 instances of inspiration. The methods described herein do no need to deliver (e.g., 620) cardiac pacing pulses in each of the 5 instances of inspiration. Rather, the methods can be completed by delivering the prescribed number of pacing pulses in the respiratory phase of interest (inspiration) over the course of many cycles (e.g., 100 cycles). In this way, during some breathing cycles only cardiac support pacing is delivered and none of the pace pulses are intended as testing for phrenic nerve activation. Continuing with the example above, in may be that only 1 cardiac pacing pulse is delivered during inspiration over the course of the 5 breath cycles. In some cases, cardiac pacing pulses are delivered during several of the 5 inspiration phases, but only 1 of them is part of the test for phrenic nerve activation, wherein an accelerometer signal is analyzed for phrenic nerve stimulation only in association with this 1 test pulse. In some embodiments, a detection window is opened only in response to a pacing pulse that is considered to be part of the test.

In some embodiments, all respiratory cycle phases are of interest, such that at least one pulse will need to be delivered 620 in each of inspiration, peak inspiration, expiration, and non-breathing phases to satisfy step 640 for a certain number of occurrences of these phases. However, in some other embodiments, not all respiration cycle phases will be of interest. For example, in some embodiments only inspiration and expiration, or peak inspiration, will be determined to be the phase or phases of interest, and in such embodiments step 640 would only check whether sufficient number of pulses (e.g., 1, 5, or 10) were delivered 630 coinciding with the phase or phases of interest.

In some embodiments, step 640 will only be satisfied when a predetermined number of pulses have been delivered in each respiratory phase of interest. For example, a device could be programmed to check for phrenic nerve activation 650 only after 10 pulses have been delivered in each respiratory phase of interest (e.g., check whether any of the previously delivered 10 pulses activated the phrenic nerve). Such embodiments allow for repeatedly testing specific pacing parameters during one or more respiratory phases of interest, which in some circumstances may produce more reliable results then testing pacing parameters a fewer number of times.

As discussed above, step 640 represents a check to determine whether a sufficient number of pulses having been delivered in satisfaction of predetermined criteria, where if not enough pulses have been delivered 620 then the method 600 continues or resumes delivering 620 cardiac pacing pulses according to the cardiac pacing schedule while holding pacing energy parameters constant until the criteria are satisfied. In this way, the method 600 essentially dwells at the current pacing parameter over one or more respiratory cycles and delivers 620 pacing pulses during various cycle phases to determine the influence of respiratory phase on phrenic nerve activation until pacing pulse parameter settings are found that reliably do not activate the phrenic nerve.

If phrenic nerve activation is detected 650 for any of the delivered 620 pulses, then the method 600 decrements 660 the current pacing pulse parameter setting. For example, if the current pacing pulse parameter setting was 1.6 volts at delivery 620, and phrenic nerve activation was detected 650 (e.g., phrenic nerve activation associated with one or more pulses delivered 620 during peak inspiration), then the pulse voltage setting can be decremented to 1.5 volts. Other parameters (e.g., pulse duration) can be scanned and decremented (or incremented in scan-up embodiments) in different amounts.

Steps 620-630-640-650-660 can be executed in a loop, decrementing 660 the pacing parameter with each turn of the loop, until phrenic nerve activation is lost for all respiration cycle phases of interest. When phrenic nerve activation is detected 650 to be lost for all respiration cycle phases of interest, the parameter levels to which the cardiac pacing parameters were decremented 660 to can be set 670 as cardiac pacing parameters for subsequent therapy (or a further decremented value can be used to provide a safety margin). The set 670 cardiac pacing parameters can then be used for therapy delivery, which provides some assurance that phrenic nerve stimulation is unlikely. The method 600 can then be initiated once again as discussed above, such as by the detection of phrenic nerve stimulation months or years after the cardiac pacing parameters have been set 670 and used for therapy.

In the method 600 of FIG. 6, the pacing pulses are delivered 620 according to a cardiac pacing schedule, such that a regimen of cardiac paces consistent with a prescribed cardiac therapy is maintained throughout testing for phrenic nerve activation. In this way, the coinciding of pulses and respiratory phases of interest occurs randomly, as alignment depends on the cardiac pacing schedule (which itself could be based on one or more physiologic parameters such as intrinsic atrial activity and/or patient activity level) and natural patient breathing. In this way, the timing of cardiac pacing pulse delivery is not based on the respiration cycle of the patient. In some other embodiments, the pulses can be delivered 620 in a manner specifically timed for the monitored 610 phases of interest, such as by changing an artioventricular delay. However, the method 600 as illustrated dwells in steps 620-640 through enough respiratory cycles until pulses are delivered during all phases of interest, wherein no pulse timing adjustment is made based on respiration (i.e. the pulse timing is dependent on cardiac parameters, such as the normal course of cardiac resynchronization therapy, and not respiratory parameters).

Figure 7:
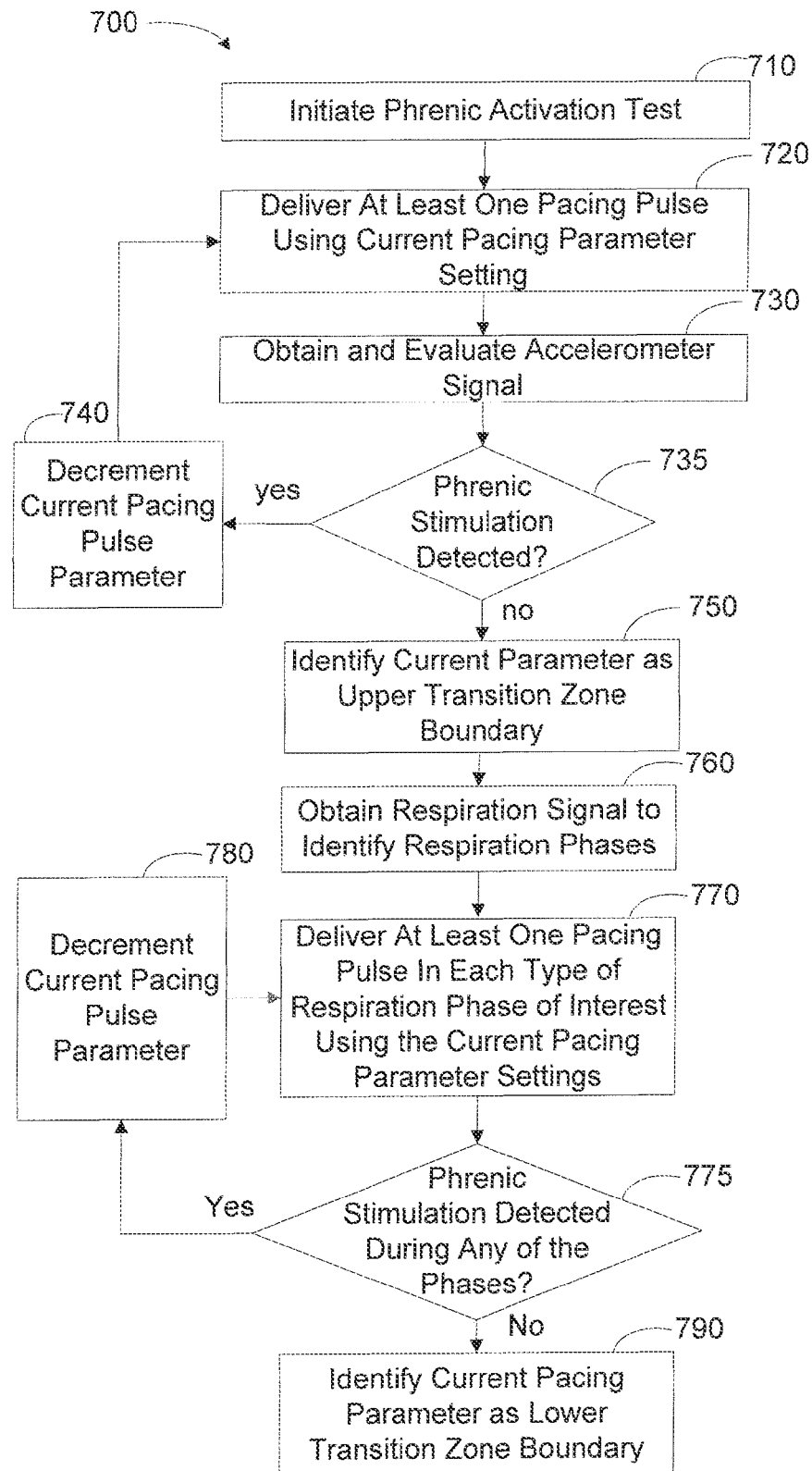
FIG. 7 is a flowchart illustrating a method of characterizing phrenic nerve activation in accordance with embodiments of this disclosure.

FIG. 7 illustrates a method 700 for characterizing a patient's phrenic nerve activation transition zone. The method 700 includes initiating 710 a phrenic nerve activation test. Initiation 710 can occur in the same manner as in the method 600 of FIG. 6 (e.g., sensing phrenic nerve stimulation).

Part of initiating 710 can include setting a current parameter level. The method 700 of FIG. 7 is generally directed to a step-down test, although the method 700 could be adapted to a step-up test. The method 700 further includes delivering 720 at least one pacing pulse to the heart using the current pacing parameter settings, which can be the levels set in the initiation 710. During and/or after delivery 720, accelerometer signals can be obtained and evaluated 730. Although step 720 pertains to the use of accelerometer signals, any type of signal that indicates phrenic nerve activation can additionally or alternatively be used. The accelerometer signal can be evaluated in any manner discussed herein to detect phrenic nerve activation 735 (e.g., in the manner of FIGS. 3-4).

If phrenic nerve activation is not detected 735, the method 700 advances to step 750. If phrenic nerve stimulation is detected, the method 700 advances to step 740 where the current pacing parameter level is decremented (e.g., reduced in voltage and/or pulse duration). In this way, the method 700 can loop through steps 720-730-735-740 until phrenic nerve activation is not detected 735 and an upper transition zone boundary is identified 750 (e.g., the upper transition zone boundary is identified as the parameter level at which phrenic nerve activation is first lost in a step-down scan).

In the embodiment of FIG. 7, respiration phase becomes particularly important once the decrementing scan reaches the upper transition boundary, as within the transition zone phrenic nerve activation becomes dependent on the respiratory cycle phase. As such, respiration signals are obtained 760 to identify respiration phases, such as using the techniques discussed herein. Such signals may include impedance, among other signals. Respiration signals can be obtained 760 at any time during the method 700, including during step 770.

In step 770, a least one cardiac pacing pulse is delivered in each type of respiration phase of interest using the current pacing parameter setting. For example, the phases of interest may be inspiration, peak inspiration, and expiration. Occurrence of these phases is identified based on the obtained 760 respiration signals. The goal is not to deliver a pacing pulse during each occurrence of these phases for each respiratory cycle, but rather to complete step 770 by at some point delivering one pacing pulse during one occurrence of each phase of interest, even if over many respiratory cycles. For example, if the phases of interest are inspiration, peak inspiration, and expiration, then step 770 could be complete when a first pulse is delivered during one instance of inspiration, a second pulse is delivered during one instance of peak inspiration, and a third pulse is delivered during one instance of expiration. It may take many respiration cycles while a device dwells at the current pulse parameter settings before the opportunity arises for a device to deliver the necessary pulses to complete step 770.

There are various ways to deliver a least one pacing pulse in each type of respiration phase of interest using the current pacing parameter setting. For example, the timing of the pace pulses of step 770 could be based on a cardiac therapy schedule, where the pacing parameters energy levels are held constant during normal pacing operation until cardiac pulses just happen to be delivered in each type of respiration phase of interest. Again, it may take many respiration cycles before the respiration phases of interest and cardiac therapy schedule naturally align. Waiting for alignment in this way can be safer for a patient, as this method prioritizes proper and consistent cardiac therapy over deviating from a cardiac therapy schedule to expedite completion of the scan.

In some other embodiments, pacing pulse timing parameters, such as atrioventricular (AV) and left ventricular-right ventricular (VV) timing parameters, can be adjusted to cause alignment of a pacing pulse and a respiration phase of interest to complete step 770 (e.g., adjusting a cardiac therapy schedule to force alignment of a pulse and a respiratory cycle phase of interest). In some cases, a device may wait for natural alignment (e.g., according to a cardiac therapy schedule based on cardiac parameters and not based on respiration), but if a timer expires without completion of step 770, then the AV delay or some other timing parameter may be slightly adjusted to force alignment.

During step 770, accelerometer or other data indicative of phrenic nerve activation can be taken and evaluated as in the manner of step 730. Using this data, it can be determined whether phrenic nerve activation was detected 775 during any of the respiratory phases of interest corresponding to a delivered 770 pacing pulse. If phrenic nerve activation was detected 775 for any of the phases of interest in which a pacing pulse was delivered 770, then the current pacing parameter is decremented 780 and step 770 is repeated. In this way, steps 770-775-780 can be repeated in a loop until a lower transition zone boundary is identified 790. Identification 790 of the lower transition zone boundary is based on the current pacing parameter settings when no phrenic nerve activation was detected 775 from pacing pulses from 770.

In some embodiments, a set of cardiac pacing pulses (i.e. a predetermined number of pulses having common energy parameters) must be delivered 770 during each type of respiratory phase of interest without any pulses of the set activating the phrenic nerve. Successive sets of pulses decreasing in energy can be delivered until all of the pulses of one of the sets do not cause phrenic nerve activation (e.g., 10 pulses must be delivered 770 during 10 occurrences of each type of phase of interest to satisfy step 770). For the energy parameters of the set that did not activate the phrenic nerve, it can be determined that the parameters are below the lower transition zone boundary 790. Sets of cardiac pacing pulses can also be used in the same manner in the other methods discussed herein (e.g., the methods of FIGS. 2 and 6).

In the method 700 of FIG. 7, a scan is conducted of one or more cardiac pacing pulse parameters in steps 720-730-735-740 without regard to respiration phase because phrenic nerve activation is not supposed to be respiration phase dependent above the transition zone. Once the upper transition zone boundary is identified 750, the subsequent scanning takes into account respiratory phase until the lower zone boundary is identified 790, because phrenic nerve activation is respiratory phase dependent within the transition zone. Although not illustrated, subsequent scanning below the lower transition zone boundary (e.g., step-down scan to identify the cardiac capture threshold) may not take into account respiratory phase, because phrenic nerve activation should not be dependent on respiratory phase below the lower transition zone boundary.

Some patients may not have a transition zone. In such cases, a device could carryout the methods discussed herein by equating the upper boundary with the lower boundary and this value would be deemed the phrenic nerve activation threshold. Some embodiments may not seek to define both an upper and lower limit of a transition zone. For example, in a scan-down embodiment, only the lower zone boundary may be of interest, such that cardiac therapy pacing parameters can be set below the lower zone boundary once the lower zone boundary is found. Some embodiments may not seek to identify transition zone boundaries, but instead just check whether phrenic nerve activation is dependent on respiration phase for a pacing parameter level of interest by testing all respiration phases of interest at the pacing parameter level of interest (e.g., as if only steps 770-775-780 were performed).

The methods and devices disclosed herein can characterize a transition zone within a strength-duration relationship. Cardiac capture is produced by pacing pulses having sufficient energy to produce a propagating wavefront of electrical depolarization that results in a contraction of the heart tissue. Generally speaking, the energy of the pacing pulse is a product of two energy parameters—the amplitude of the pacing pulse and the duration of the pulse. Thus, the capture threshold voltage over a range of pulse widths may be expressed in a capture strength-duration plot 810 as illustrated in FIG. 8.

Phrenic nerve activation by a pacing pulse is also dependent on the pulse energy. The phrenic nerve activation strength-duration plot 820 for reliable undesirable activation may have a different characteristic from the capture strength-duration plot 810 and may have a relationship between pacing pulse voltage and pacing pulse width.

Figure 8:
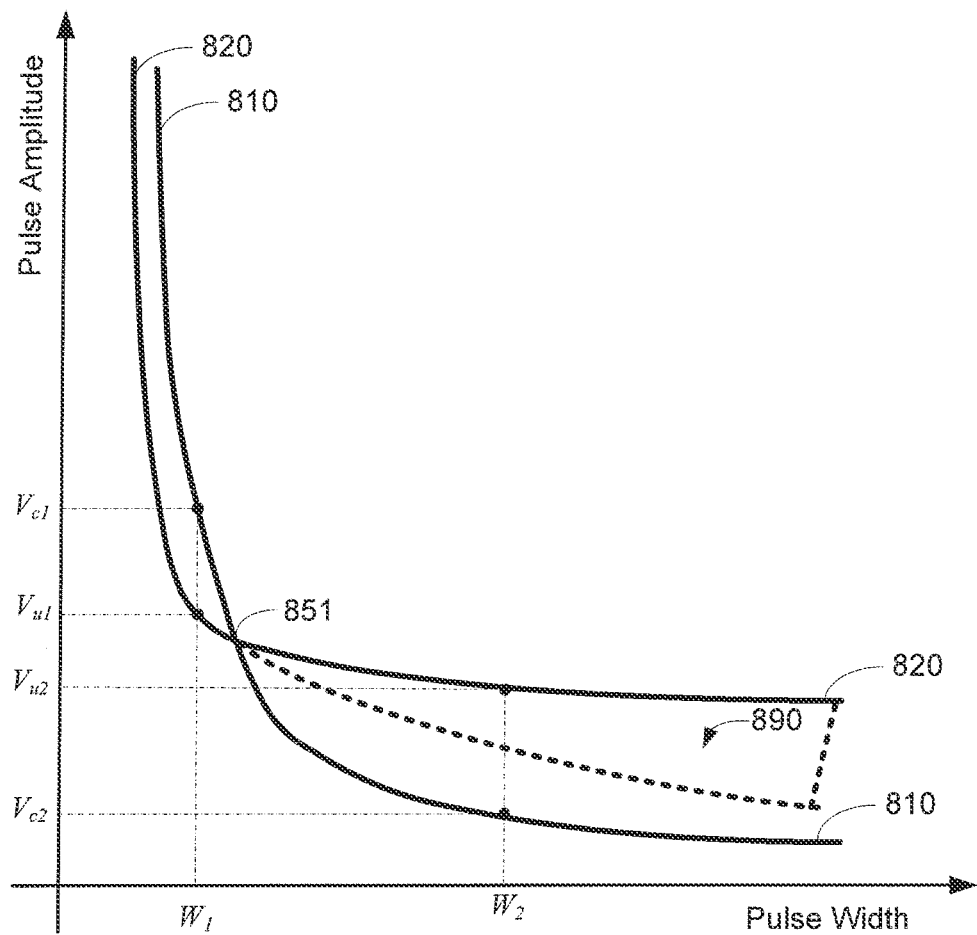
FIG. 8 is a graph illustrating various aspects of strength-duration pacing pulse parameters and a transition zone in accordance with embodiments of this disclosure.

FIG. 8 provides graphs illustrating a capture strength-duration plot 810 associated with cardiac capture and a phrenic nerve activation strength-duration plot 820 associated with reliable undesirable diaphragmic activation (e.g., phrenic nerve activation regardless of respiratory phase). A pacing pulse having a pulse width of $W_1$ requires a pulse amplitude of $V_{c1}$ to produce capture. A pacing pulse having pulse width $W_1$ and pulse amplitude $V_{c1}$ exceeds the voltage threshold, $V_{u1}$, for an undesirable diaphragmic activation through phrenic nerve stimulation. If the pulse width is increased to $W_2$, the voltage required for capture, $V_{c2}$, is less than the voltage required for undesirable diaphragmic activation, $V_{u2}$. Therefore, pacing pulses can be delivered at the pacing energy associated with $W_2$, $V_{c2}$ to provide capture of the heart without causing the phrenic nerve activation.

The area to the right of the intersection 851 of the capture and phrenic nerve activation strength-duration plots 810, 820, between the phrenic nerve activation strength-duration 820 and capture strength-duration 810 plots, defines a set of energy parameter values that produce capture while avoiding phrenic nerve activation. Pacing pulses within this region produce a more ideal therapy response (capture without undesirable stimulation).

The capture and phrenic nerve activation strength-duration plots 810, 820 of FIG. 8 may be generated by delivering a number of test pulses at various amplitudes and pulse widths and evaluating whether cardiac capture and undesirable stimulation occurred (e.g., using the methods of FIGS. 1, 6, and/or 7). The capture and phrenic nerve activation strength-duration plots 810, 820 can then be completed by interpolation and extrapolation based on, for example, an exponential fit. Such methods can minimize the number of test pulses required to fully characterize the relationships between pulse parameters and stimulation, thereby minimizing battery consumption and uncomfortable testing. Extrapolation and interpolation can also allow the relationships between pulse parameters and stimulation for a particular device configuration to be characterized beyond what the device itself is programmed to, or capable of, performing. Methods and systems for determining and using strength-duration relationships are described in U.S. Pat. No. 8,209,013, which is incorporated herein by reference in its entirety.

FIG. 8 also illustrates a transition zone 890 outlined by dashed lines and the phrenic nerve activation strength-duration plot 820. The transition zone 890 is the parameter range inside of which phrenic nerve activation is dependent on the phase of the patient's respiration cycle. The transition zone 890 could be determined by scanning techniques, such as by the method of FIG. 7 performed for both pulse voltage and duration parameters.

In programming a therapy device, it is generally desirable to program a pacing device so as to not risk causing undesirable stimulation, such as phrenic nerve activation. Therefore, it can be desirable to select pacing parameters that are not within a transition zone. Moreover, it can be desirable to select pacing parameter settings below a transition zone because the lower the pulse voltage and pulse duration the less battery energy is used for therapy. These aspects of therapy programming can make use of a strength-duration curve and transition zone, such as that of FIG. 8.

For example, a doctor or system analyzing FIG. 8 may select a pacing pulse parameter (e.g., voltage) above the capture strength-duration plot 810 but below the transition zone 890 as a setting that will reliably capture the appropriate chamber (e.g., left ventricle) without occasionally activating the phrenic nerve.

A doctor or system may select a voltage parameter based on the voltage range above the capture strength-duration plot 810 and below the transition zone 890. For example, some pacing protocols will vary the pulse voltage between pulses for various reasons during the normal course of therapy. A greater parameter range between capture strength-duration plot 810 and the transition zone 890 indicates a greater parameter range within which a protocol (e.g., automatic ventricular capture test) has to operate to vary a parameter (e.g., pulse voltage). In the case of FIG. 8, a doctor or system may be more likely to select a shorter pulse width because the shorter pulse widths are associated with a greater range between the capture strength-duration plot 810 and the transition zone 890 relative to longer pulse widths. In this way, a doctor or system can select a pacing pulse parameter level (e.g., voltage or duration) based on that parameter level having a greater range between a transition zone and a threshold (e.g., cardiac capture or phrenic nerve activation threshold) relative to other parameter levels.

If a doctor or system wanted or needed to use a parameter setting within a transition zone (e.g., if preferred therapy parameters were only possible within a transition zone) then the methods described herein could inform the doctor that the device would need to be programmed to time pacing pulses (e.g., left ventricular pulses) with the respiration cycle to minimize phrenic nerve activation by avoiding delivering pulses when the respiration cycle is in the phase most susceptible to phrenic nerve activation identified for that particular patient and pace pulse settings (e.g., vector and energy parameters) using the methods and systems discussed herein. In some embodiments, a system could automatically avoid delivering pulses during respiratory phase or phases that are identified by the methods and systems discussed herein as most susceptible to phrenic nerve activation for a particular patient.

Multiple strength-duration plots having transition zones like the one illustrated in FIG. 8 can be generated for multiple different electrode combinations. Based on the strength-duration plots, a preferred electrode combination can be selected for delivering therapy. For example, if one electrode combination is associated with a smaller transition zone then it may be preferable to select for therapy delivery versus an electrode combination having a larger transition zone. In many cases, the electrode combination with the smaller transition zone would likely correspond to the configuration having the greatest amount of flexibility in an operation that achieves a desired therapy outcome (e.g., capture without phrenic nerve activation). Parameter and electrode selection in the ways described herein may be performed by a human or automatically by a processor executing stored program instructions. Methods and systems for electrode combination selection are described in U.S. Pat. No. 8,265,736, which is incorporated herein by reference in its entirety.

In some embodiments, a preferred electrode combination for delivering pacing therapy can be selected (e.g., by a human or controller) on the basis of which combination has the greatest range between the capture strength-duration plot 810 and the detected pacing settings at which phrenic nerve activation is not detected for any respiratory phases (e.g., as determined by the methods of FIGS. 1, 6, and/or 7). Selecting on the basis of such a range gives an automated therapy program the most range in which to modify a parameter (e.g., voltage) as needed over time.

Various embodiments not only test various energy parameters to characterize a patient's phrenic nerve activation response, but also test various electrode combinations used for pace pulse delivery. For example, an embodiment according to FIG. 6 could additionally or alternatively switch electrode combinations for step 660, cycling through various electrode combinations by repeating steps 620-620-640-650-660 until a vector is found that is not associated with phrenic nerve activation for any phases of respiration. An electrode combination can then be selected and used for cardiac therapy delivery based on which electrode combination has preferable energy parameters (e.g., lowest capture threshold) that is not associated with phrenic nerve activation for any phases of respiration at those preferable energy parameters. The other embodiments discussed herein (e.g., FIGS. 1-10) can likewise test different electrode combinations and facilitate vector selection based on which vector or vectors provide a beneficial therapeutic response using preferable energy parameters that are not associated with phrenic nerve activation for any phases of respiration at those preferable energy parameters.

In some embodiments, the particular phase or phases of a patient's respiration cycles in which phrenic nerve stimulation occurs can be identified. For example, only during certain phases of the respiratory cycle are some patients particularly susceptible to phrenic nerve stimulation at certain pacing parameter settings. As such, various embodiments can determine which respiratory phase(s) are associated with phrenic nerve activation and which are not, such as by using the methods described herein in connection with FIGS. 1-10. Therefore, pacing pulses can only be delivered during those phases which are not associated with phrenic nerve stimulation and/or pacing therapy timing parameters can be adjusted (e.g., artioventricular delay and/or biventricular delay) can be automatically adjusted as needed to avoid delivering a pacing pulse during a respiratory phase determined to be associated with phrenic nerve stimulation.

The methods and techniques described herein can be used to identify different thresholds for different respiration phases. For example, the scanning aspects of FIGS. 1, 6, and/or 7 can be used to identify a phrenic nerve activation threshold for each phase of interest, such as inspiration, peak inspiration, expiration, and non-breathing, by delivering cardiac pacing pulse during these phases and scanning across one or more pulse energy parameters. For example, FIG. 1 can be used to determine at which voltage a patient's phrenic nerve will be activated by a cardiac pacing pulse delivered during inspiration. The same can be done for the other respiratory phases, such that 4 different phrenic nerve activation thresholds will be identified, one for each phase of respiration. This information can then be used for therapy delivery. For example, the 4 phrenic nerve activation thresholds can be automatically programmed for use during CRM therapy delivery. During therapy delivery a device can monitor respiratory phase, and depending on which respiratory phase a patient is in when it is desired to deliver a cardiac pacing pulse, pulse energy level can be varied in accordance with the phrenic nerve activation threshold of the current respiratory phase. Considering that heart rate is typically faster than respiratory rate, several cardiac pacing pulses could be delivered during a single respiratory cycle, the energy level of each pulse adjusted to be below the phrenic nerve activation threshold of the current respiratory phase.

A cardiac rhythm management system configured to carry out such methods can comprise an implantable cardiac pacing device having a plurality of electrodes configured for implantation in a patient; circuitry configured to output a plurality of cardiac pacing pulses through the electrodes and modify one or more pacing parameters of the plurality of cardiac pacing pulses; a phrenic nerve activation sensor configured to output a phrenic nerve activation signal indicative of activation of the patient's phrenic nerve; a respiration sensor configured to output a respiration signal indicative of inhalation and exhalation respiratory activity of the patient; and a controller configured to execute program instructions stored in memory to cause the system to identify a plurality of different respiratory phases based on the respiration signal for multiple respiratory cycles of the patient, deliver the plurality of cardiac pacing pulses within each of the identified plurality of different respiratory phases, analyze the phrenic nerve stimulation signal to identify respective phrenic nerve activation thresholds for a plurality of different respiratory phases based on the phrenic nerve activation signal, identify cardiac pacing pulse parameters for each of the plurality of respiratory phases based on the respective phrenic nerve activation thresholds for the plurality of respiratory phases, and deliver a cardiac pacing pulse therapy by varying pulse energy output based on which respiratory phase each pacing pulse of the therapy is to be delivered in using the identified cardiac pacing pulse parameters.

Figure 9:
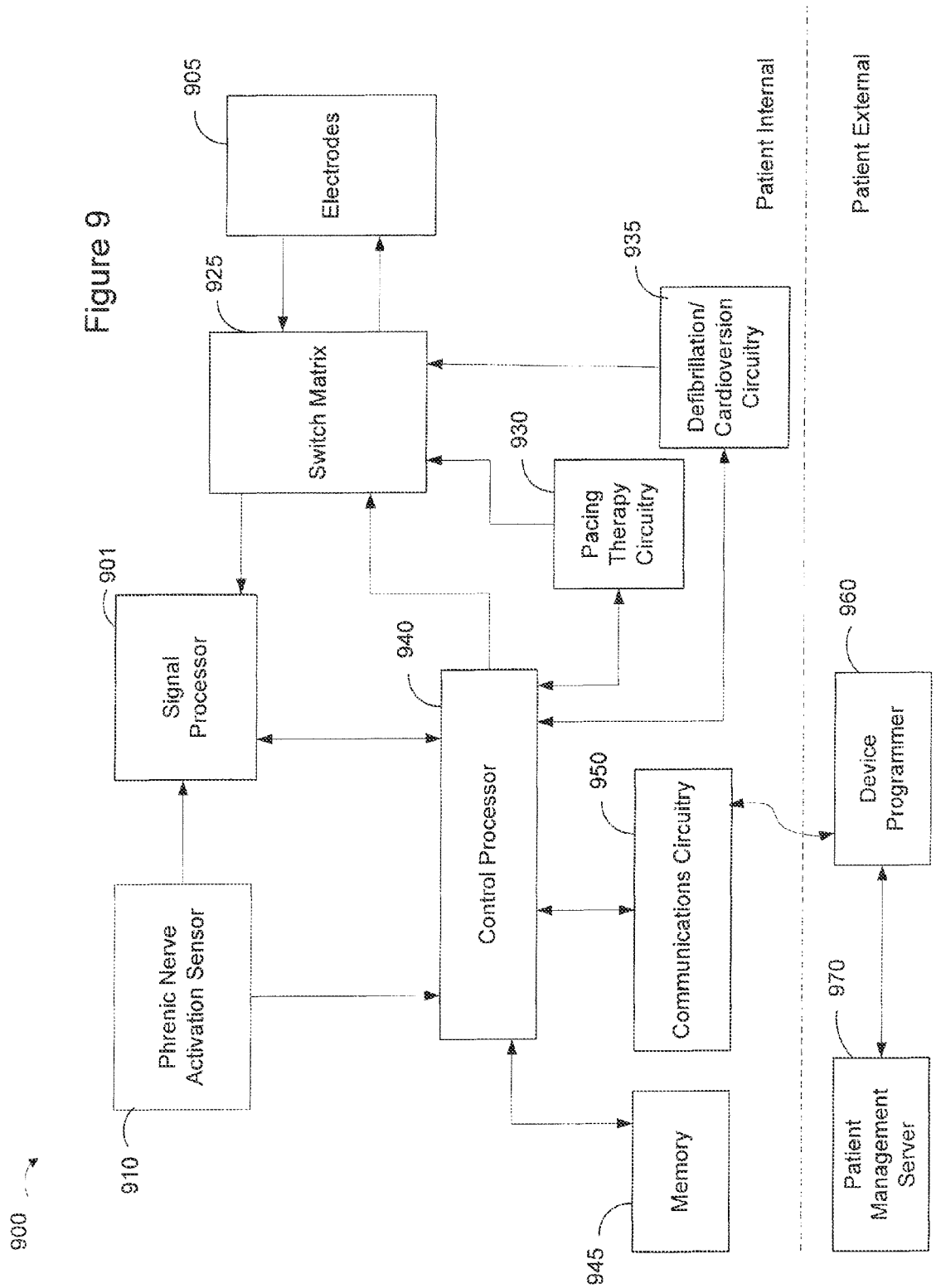
FIG. 9 is a block diagram of a system incorporating phrenic nerve activation characterization and avoidance circuitry in accordance with embodiments of this disclosure.

FIG. 9 is a block diagram of a CRM device 900 that may incorporate circuitry employing phrenic nerve activation detection algorithms in accordance with embodiments of the present invention. The CRM device 900 includes pacing therapy circuitry 930 that delivers pacing pulses to a heart. The CRM device 900 may optionally include defibrillation/cardioversion circuitry 935 configured to deliver high energy defibrillation or cardioversion stimulation to the heart for terminating dangerous tachyarrhythmias.

The pacing pulses are delivered via multiple cardiac electrodes 905 (using electrode combinations), which can be disposed at multiple locations within a heart, among other locations. Two or more electrodes may be disposed within a single heart chamber, such as the left ventricle. The electrodes 905 are coupled to switch matrix 925 circuitry used to selectively couple electrodes 905 of various pacing configurations to signal processor 901, pacing therapy circuitry 930, defibrillation/cardioversion circuitry 935, and/or other components of the CRM device 900.

The CRM 900 device also includes a phrenic nerve activation sensor 910. The phrenic nerve activation sensor 910 can output a signal and/or other information to signal processor 901 and control processor 940. Phrenic nerve activation sensor 910 may include an accelerometer, electrical signal sensors (e.g., EMG, impedance), pressure sensor, acoustic sensors, and/or any other sensor that can detect phrenic nerve activation. Phrenic nerve activation sensor 910 may be implemented using a discrete sensor or via software executed by a processor (e.g., control processor 940) of the CRM device.

The control processor 940 can use information received from the signal processor 901, the phrenic nerve activation sensor 910, memory 945, and other components to implement phrenic nerve activation characterization and avoidance algorithms, as disclosed herein.

For example, the pacing therapy circuitry 930 can provide information regarding when a pacing pulse was delivered and the parameters of the pacing pulse, the phrenic nerve activation sensor 910 can provide information regarding sensed phrenic nerve activation, and signal processor 901 can provide information regarding transthoracic impedance (measured between electrodes 905). This information can be used to identify respiratory cycle phases, phrenic nerve activation, phrenic nerve activation transition zones, and manage therapy delivery to avoid phrenic nerve activation, among other things.

Amplitude, peak timing, and/or correlation of delivered pulses to phrenic nerve activation (beat-to-beat and/or over time) can be used with a phrenic nerve activation signal in either the time or frequency domain to determine whether one or more pacing pulses caused phrenic nerve stimulation.

A CRM device 900 typically includes a battery power supply (not shown) and communications circuitry 950 for communicating with an external device programmer 960 or other patient-external device. Information, such as data, parameter information, evaluations, comparisons, data, and/or program instructions, and the like, can be transferred between the device programmer 960 and patient management server 970, CRM device 900 and the device programmer 960, and/or between the CRM device 900 and the patient management server 970 and/or other external system. In some embodiments, the processor 940, memory 945, and/or signal processor 901 may be components of the device programmer 960, patient management server 970, and/or other patient external system.

The CRM device 900 also includes memory 945 for storing executable program instructions and/or data, accessed by and through the control processor 940. In various configurations, the memory 945 may be used to store information related to thresholds, parameters, measured values, transitions zones, phrenic nerve activation patterns, program instructions, and the like.

The circuitry represented in FIG. 9 can be used to perform the various methodologies and techniques discussed herein. Memory 945 can be a computer readable medium encoded with a computer program, software, firmware, computer executable instructions, instructions capable of being executed by a computer, etc. to be executed by circuitry, such as control processor 940. For example, memory 945 can be a computer readable medium storing a computer program, execution of the computer program by control processor 940 causing delivery of pacing pulses directed by the pacing therapy circuitry, reception of one or more signals from phrenic nerve activation sensors 910 and/or signal processor 901 to identify phrenic nerve activation transition zones and manage therapy parameters to avoid phrenic nerve activation in accordance with the various methods and techniques made known or referenced by the present disclosure. In similar ways, the other methods and techniques discussed herein can be performed using the circuitry represented in FIG. 9.

The methods and devices discussed herein can collect electrical signals, such as impedance signals indicative of respiration and electrical cardiac signals indicative of heart activity, using electrodes. Such electrodes can include implanted electrodes 905 and/or external electrodes, such as skin electrodes (not shown).

Figure 10:
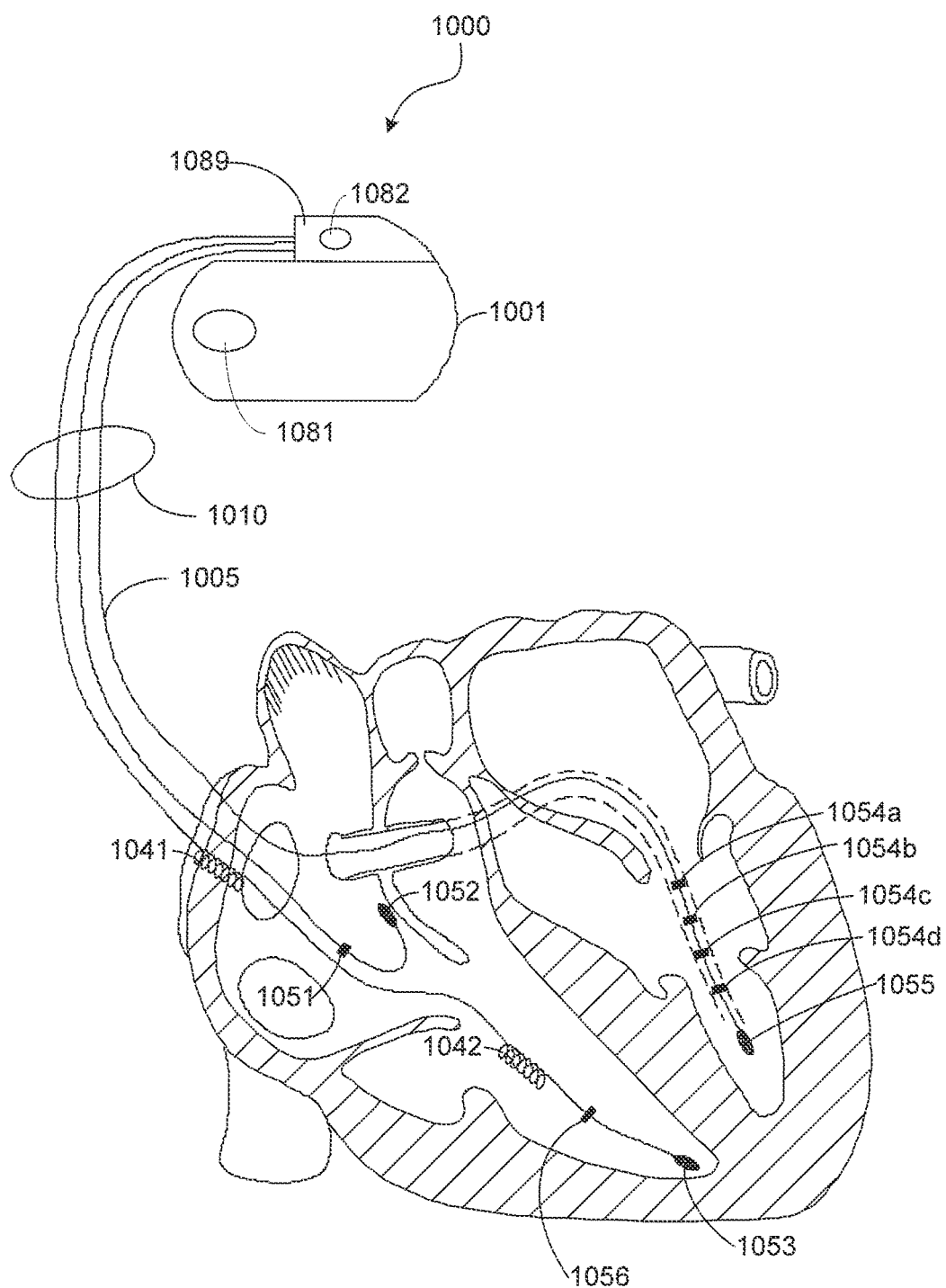
FIG. 10 is a diagram illustrating a patient-internal device in accordance with embodiments of this disclosure.

The therapy device 1000 illustrated in FIG. 10 employs circuitry capable of implementing phrenic nerve activation detection algorithm techniques described herein. The therapy device 1000 includes CRM circuitry enclosed within an implantable housing 1001. The CRM circuitry is electrically coupled to an intracardiac lead system 1010. Although an intracardiac lead system 1010 is illustrated in FIG. 10, various other types of lead/electrode systems may additionally or alternatively be deployed. For example, the lead/electrode system may comprise an epicardial lead/electrode system including electrodes outside the heart and/or cardiac vasculature, such as a heart sock, an epicardial patch, and/or a subcutaneous system having electrodes implanted below the skin surface but outside the ribcage.

Portions of the intracardiac lead system 1010 are shown inserted into the patient's heart. The lead system 1010 includes cardiac pace/sense electrodes 1051-1056 positioned in, on, or about one or more heart chambers for sensing electrical signals from the patient's heart and/or delivering pacing pulses to the heart. The intracardiac sense/pace electrodes, such as those illustrated in FIG. 10, may be used to sense and/or pace one or more chambers of the heart, including the left ventricle, the right ventricle, the left atrium and/or the right atrium. The CRM circuitry controls the delivery of electrical stimulation pulses delivered via the electrodes 1051-1056. The electrical stimulation pulses may be used to ensure that the heart beats at a hemodynamically sufficient rate, may be used to improve the synchrony of the heart beats, may be used to increase the strength of the heart beats, and/or may be used for other therapeutic purposes to support cardiac function consistent with a prescribed therapy while avoiding phrenic nerve activation.

The lead system 1010 may include defibrillation electrodes 1041, 1042 for delivering defibrillation/cardioversion pulses to the heart.

The left ventricular lead 1005 incorporates multiple electrodes 1054a-1054d and 1055 positioned at various locations within the coronary venous system proximate the left ventricle. Stimulating the ventricle at multiple locations in the left ventricle or at a single selected location may provide for increased cardiac output in patients suffering from heart failure (HF), for example, and/or may provide for other benefits. Electrical stimulation pulses may be delivered via the selected electrodes according to a timing sequence and output configuration that enhances cardiac function. Although FIG. 10 illustrates multiple left ventricle electrodes, in other configurations, multiple electrodes may alternatively or additionally be provided in one or more of the right atrium, left atrium, and right ventricle.

Portions of the housing 1001 of the implantable device 1000 may optionally serve as one or more multiple can 1081 or indifferent 1082 electrodes. The housing 1001 is illustrated as incorporating a header 1089 that may be configured to facilitate removable attachment between one or more leads and the housing 1001. The housing 1001 of the therapy device 1000 may include one or more can electrodes 1081. The header 1089 of the therapy device 1000 may include one or more indifferent electrodes 1082. The can 1081 and/or indifferent 1082 electrodes may be used to deliver pacing and/or defibrillation stimulation to the heart and/or for sensing electrical cardiac signals of the heart. One or more accelerometers can be provided on and/or within the housing 1001, header 1001, or lead system 1010 for sensing phrenic nerve activation.

Communications circuitry is disposed within the housing 1001 for facilitating communication between the CRM circuitry and a patient-external device, such as an external programmer or advanced patient management (APM) system. The therapy device 1000 may also include sensors and appropriate circuitry for sensing a patient's metabolic need and adjusting the pacing pulses delivered to the heart to accommodate the patient's metabolic need.

Impedance can be measured to track respiration phases. In some embodiments, measurement of impedance involves an electrical stimulation source, such as an exciter. The exciter delivers an electrical excitation signal, such as a strobed sequence of current pulses or other measurement stimuli, to the heart between the electrodes. In response to the excitation signal provided by an exciter, a response signal, e.g., voltage response value, is sensed by impedance detector circuitry, such as that in a signal processor. From the measured voltage response value and the known current value, the impedance of the electrode combination may be calculated.

For example, a small current can be injected through electrodes 905 (of FIG. 9) by pacing therapy circuitry 930 or other components. The impedance between two or more electrodes 905 is then measured, changes in which can reflect the phases of respiration as shown in FIG. 2. The electrodes could be skin surface electrodes or subcutaneous electrodes. Different electrode pairs could be used. For example, any pair or grouping of electrodes of FIG. 10 can be used to measure impedance, including lead-to-lead (e.g., 1055-1041), lead-to-can (e.g., 1053-1081), and can-to-can (e.g., 1081-1082) measurements.

Techniques and circuitry for determining the impedance of an electrode combination is described in commonly owned U.S. Pat. No. 6,076,015 which is incorporated herein by reference in its entirety.

In some implementations, an APM system may be used to perform some of the processes discussed herein, including evaluating, estimating, comparing, detecting, selecting, and updating, among others. Methods, structures, and/or techniques described herein, may incorporate various APM related methodologies, including features described in one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference in each of their respective entireties.

In certain embodiments, the therapy device 1000 may include circuitry for detecting and treating cardiac tachyarrhythmia via defibrillation therapy and/or anti-tachyarrhythmia pacing (ATP). Configurations providing defibrillation capability may make use of defibrillation coils 1041, 1042 for delivering high energy pulses to the heart to terminate or mitigate tachyarrhythmia.

CRM devices using multiple electrodes, such as illustrated herein, are capable of delivering pacing pulses to multiple sites of the atria and/or ventricles during a cardiac cycle. Certain patients may benefit from activation of parts of a heart chamber, such as a ventricle, at different times in order to distribute the pumping load and/or depolarization sequence to different areas of the ventricle. A multi-electrode pacemaker has the capability of switching the output of pacing pulses between selected electrode combinations within a heart chamber during different cardiac cycles.

Commonly owned U.S. Pat. No. 6,772,008, which is incorporated herein by reference, describes methods and systems that may be used in relation to detecting undesirable tissue stimulation. Muscle stimulation may be detected, for example, through the use of an accelerometer and/or other circuitry that senses accelerations indicating muscle movements (e.g., diaphragmatic) that coincide with the output of the stimulation pulse. Other methods of measuring tissue stimulation (e.g., phrenic nerve activation) may involve, for example, the use of an electromyogram sensor (EMG), microphone, and/or other sensors. For example, phrenic nerve activation may be automatically detected using a microphone to detect the patient's expiration response to undesirable diaphragmic activation due to electrical phrenic nerve activation.

Undesirable nerve or muscle stimulation may be detected by sensing a parameter that is directly or indirectly responsive to the stimulation. Undesirable nerve stimulation, such as stimulation of the vagus or phrenic nerves, for example, may be directly sensed using electroneurogram (ENG) electrodes and circuitry to measure and/or record nerve spikes and/or action potentials in a nerve. An ENG sensor may comprise a neural cuff and/or other type or neural electrodes located on or near the nerve of interest. For example, systems and methods for direct measurement of nerve activation signals are discussed in U.S. Pat. Nos. 4,573,481 and 5,658,318 which are incorporated herein by reference in their respective entireties. The ENG may comprise a helical neural electrode that wraps around the nerve (e.g., phrenic nerve) and is electrically connected to circuitry configured to measure the nerve activity. The neural electrodes and circuitry operate to detect an electrical activation (action potential) of the nerve following application of the cardiac pacing pulse.

Neural activation can be detected by sensing a surrogate parameter that is indirectly responsive to nerve stimulation. Lung pressure, pleural pressure, thoracic pressure, airway pressure, and thoracic impedance are examples of parameters that change responsive to stimulation of the phrenic nerve. In some embodiments, a patient's airway pressure may be measured during and/or closely following delivery of electrical stimulation. The detected change in pressure may be related to stimulation of the phrenic nerve.

Undesirable stimulation threshold measuring may be performed by iteratively increasing, decreasing, or in some way changing a voltage, current, duration, energy level, and/or other therapy parameter between a series of test pulses. One or more sensors can monitor for undesirable activation immediately after each test pulse is delivered. Using these methods, the point at which a parameter change causes undesirable stimulation can be identified as a stimulation threshold.

By way of example and not by way of limitation, the undesirable stimulation threshold for a particular electrode combination may be measured by delivering a first test pulse using the initial electrode combination. During and/or after each test pulse is delivered, sensors can monitor for undesirable stimulation. For example, an accelerometer may monitor for movement of the diaphragm indicating that the test pulse stimulated the phrenic nerve and/or diaphragm muscle. If no phrenic nerve and/or diaphragm muscle stimulation is detected after delivery of a test pulse, then the test pulse is increased a predetermined amount and another test pulse is delivered. This scanning process of delivering, monitoring, and incrementing is repeated until phrenic nerve and/or diaphragm muscle stimulation is detected. One or more of the test pulse parameters at which the first undesirable stimulation is detected can be considered to be the undesirable stimulation threshold.

The various steps of FIGS. 1, 6, and 7, as well as the other steps and methods disclosed herein, can be performed automatically, such that no direct human assistance (e.g., physician and/or patient) is needed to initiate or perform the various discrete steps. Alternatively, the various steps of this disclosure can be performed semi-automatically requiring some amount of human interaction to initiate or conduct one or more steps.

The various steps of FIGS. 1, 6, and 7, as well as other methods and steps discussed herein, can be initiated upon implant, by a physician, upon detection of a change in condition, and/or periodically. Condition changes that could initiate the processes include detection of phrenic nerve activation, loss of capture, change in posture, change in disease state, detection of non-therapeutic activation, and/or short or long term change in patient activity state, for example.

Periodic and/or condition initiated testing to update capture threshold, phrenic nerve activation threshold, and device relationship information can be useful to monitor for certain conditions that might not otherwise be readily apparent but warrant attention and/or a therapy change. Device and/or physiologic changes may alter the effect of pacing pulses. For example, device component defects, lead migration, electrode encapsulation, and/or physiologic changes may increase the pacing pulse amplitude needed to reliably produce capture and/or decrease the pacing pulse amplitude needed to stimulate the phrenic nerve, leading to uncomfortable and ineffective pacing therapy. Updated capture threshold, phrenic nerve activation threshold, transition zones, and device relationship information can be used to automatically reprogram the therapy device and/or alert a physician to reconfigure the therapy device.

The various processes illustrated and/or described herein (e.g., the processes of FIGS. 1, 6, and 7) can be performed using a single device embodiment configured to perform each of the processes (e.g., the circuitry of FIG. 9 in the configuration of FIG. 10) that concern the concepts illustrated and discussed in connection with FIGS. 2-5 and 8.

Sensors that can be used for detection of phrenic nerve activation are also used for rate-adaptive pacing. Rate-adaptive pacemakers are typically used to treat patients who are chronotropically incompetent. In these devices, patient activity and/or metabolic demand are determined and the patient activity/metabolic demand information can be used to control the pacing rate. A number of sensor types have been used for rate control. Motion sensors, such as accelerometers, piezoelectric sensors, and/or magnetic ball sensors, are widely used for detecting the vibration caused by patient activity. Accelerometers sense motion of the patient's body and are used in systems that have the capability to provide rapid rate responsiveness based on patent activity. However, accelerometer-based activity sensors can be fooled by motion that is not related to patient activity, such as riding in a car on a bumpy road, which may trigger inappropriate increases in pacing rate.

Although sometimes more complex than accelerometer-based activity sensors, minute ventilation (MV) sensors are also frequently used to control pacing rate. MV sensors detect patient respiration and derive from the respiration signal the amount of air moved in one minute. MV sensors offer several advantages over accelerometers because MV sensors can appropriately increase pacing rate during periods that heart rate would naturally increase without a concurrent increase in patient activity, such as during periods that the patient experiences intense emotion. Other types of sensors have also been used or proposed for rate-adaptive pacing, e.g., sensors based on QT interval, peak endocardial acceleration, pre-ejection interval, etc. Pacing rate control using multiple sensors may also be used, such as by blending the sensor outputs.

The output of a rate-adaptation sensor is used to generate a sensor indicated rate (SIR) which controls the pacing rate when the pacemaker is operating in a rate-responsive pacing mode. The output of the rate-adaptation sensor is processed with characteristics of the processing, e.g., sampling rate, gain, offset, and filtering characteristics, selected to enhance the detection of changes in activity and/or metabolic demand.

Some types of sensors used to control rate-adaptive pacing, e.g., MV sensors and accelerometers, also respond to skeletal muscle contractions caused by phrenic nerve activation. Because sensors used to control rate-adaptive pacing are already well known and are readily available in a large number of cardiac devices, it is desirable to use the same sensor for both rate-adaptive pacing control and detection of phrenic nerve stimulation. However, the signal processing requirements for optimally sensing rate-adaptation parameters, such as activity or metabolic demand, are different from the signal processing requirements for optimally detecting phrenic nerve activation.

Embodiments of the invention are directed to approaches employing a single sensor that is used both for sensing rate-adaptation parameters, such as patient activity or metabolic demand and for detecting phrenic nerve activation. The sensor signal is processed using first signal processing characteristics that are selected for optimal sensing of a rate-adaptation parameter, e.g., MV or activity. The sensor signal is processed using second signal processing characteristics that are selected for optimal phrenic nerve activation detection.

Figure 11A:
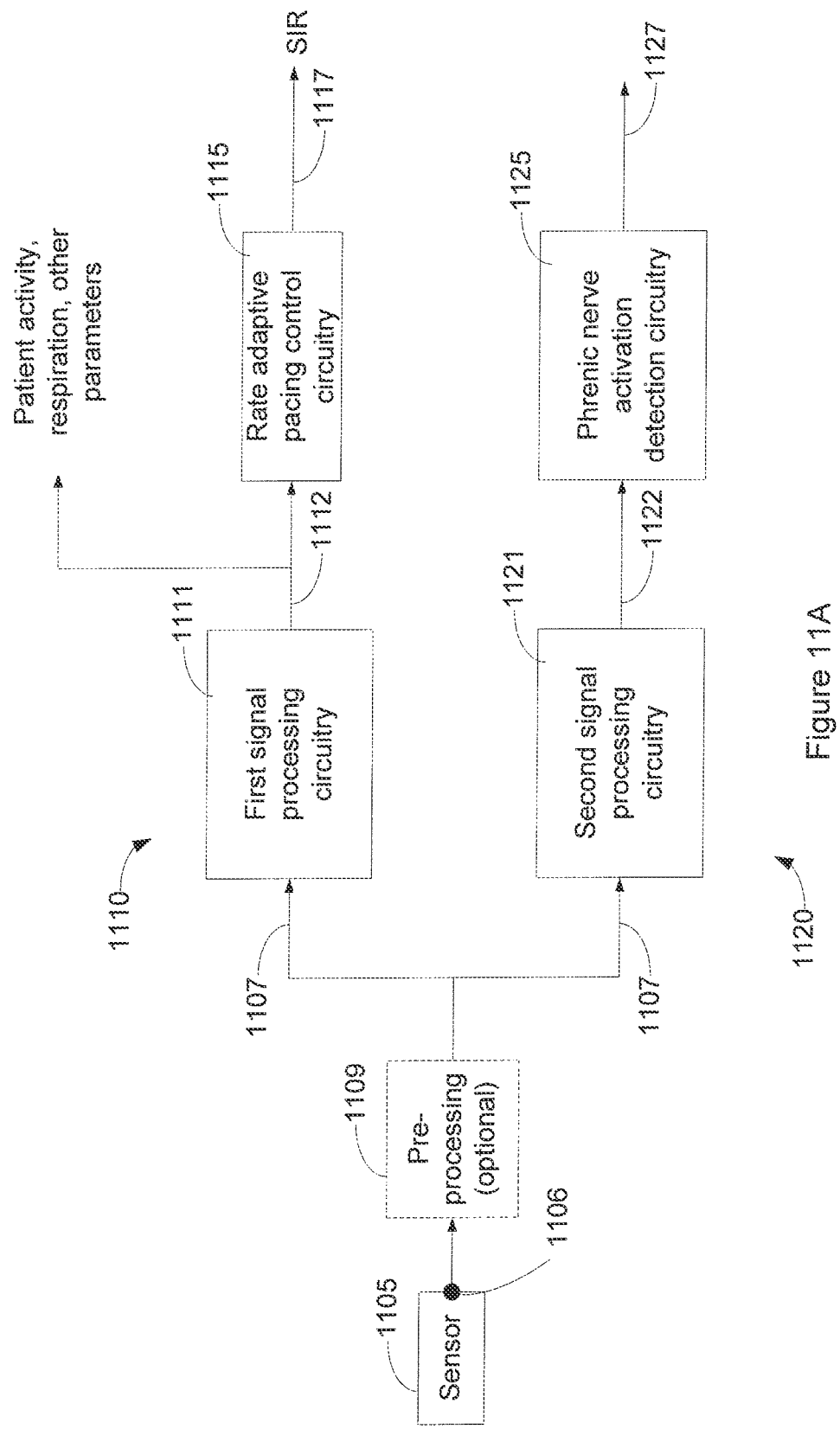
FIG. 11A is a block diagram of medical device circuitry configured to process a sensor signal output using separate signal processing channels for activity/metabolic demand sensing and phrenic nerve activation sensing in accordance with embodiments of this disclosure.

In some implementations, the sensor signal 1107 is processed using two separate signal processing channels as illustrated in FIG. 11A. The output terminal 1106 of the sensor 1105 (e.g., MV sensor, activity sensor) used to control rate-adaptive pacing is coupled to a first signal processing channel 1110 and to a second signal processing channel 1120. The first and second signal processing channels 1110, 1120 include first and second signal processing circuitry 1111, 1121, respectively. The first signal processing circuitry 1111 has a first set of signal processing characteristics that are selected for determining patient activity or metabolic demand and which are used to process the sensor signal 1107. The second signal processing circuitry 1121 has a second set of signal processing characteristics that are selected for detecting phrenic nerve activation and which are used to process the sensor signal 1107. The signal processing channels 1110, 1120 may include analog components, digital components or a mixture of analog and digital components.

In one example, the first signal processing circuitry 1111 includes one or more filters configured to attenuate certain frequencies of the sensor signal. The second signal processing circuitry 1121 may also include one or more filters configured to attenuate frequencies of the sensor signal. The filter characteristics of the first filters are different from those of the second filters. In some implementations, the first signal processing circuitry 1111 includes amplifier circuitry that has different amplifier characteristics from the amplifier characteristics of the second signal processing circuitry 1121. In some implementations, one or both of the first signal processing circuitry 1111 and the second signal processing circuitry may include an A/D converter for converting the analog sensor signal 1107 to a digital signal. The A/D conversion characteristics of the first signal processing circuitry (n-bit resolution, sampling rate, etc.) may be different from the A/D conversion characteristics of the second signal processing circuitry. In some implementations, only one of the signal processing channels 1110, 1120 includes an A/D converter, so that the signal processing performed by one of the channels 1110, 1120 is achieved predominantly by analog signal processing and the signal processing performed by the other of the channels 1120, 1110 is achieved by digital signal processing.

In some configurations, pre-processing circuitry 1109, e.g., amplifiers, analog and/or digital filter components, and/or an A/D converter may be interposed in the signal path 1107 between the sensor output terminal 1106 and the signal processing channels 1110, 1120. The pre-processing circuitry may provide A/D conversion, pre-filtering or pre-amplification functions applied to the output of the sensor to produce the signal 1107.

Consider an implementation that uses an accelerometer (e.g., single axis or multi-axis accelerometer) to determine patient activity which in turn is used to develop a sensor indicated rate (SIR) for adapting the pacing rate. As the patient engages in activity, such as running or walking, the output of the accelerometer tracks the patient movement. The modulation in the accelerometer signal caused by patient movement includes relatively low frequency components, typically between about 1 and 10 Hz. Therefore, frequencies less than about 1 Hz and greater than about 10 Hz are noise with respect to patient activity and it is desirable to remove these signals from the activity signal, such as by using a band pass filter.

On the other hand, activation of the phrenic nerve causes an abrupt contraction of the skeletal muscle of the diaphragm similar to a hiccup reflex. This abrupt contraction produces an accelerometer signal having frequency components which are greater than about 5 Hz, and are discernibly higher than the frequency components associated with patient activity signal. Thus, it is desirable to filter out lower frequencies predominantly associated with patient motion to enhance detection of the higher frequency components associated with phrenic nerve activation. If a signal processed for activity sensing is used for phrenic nerve activation, low frequency deflections in a signal filtered for activity sensing, e.g., signal spikes on the order of about 4-6 Hz, can cause erroneous phrenic nerve activation detection. Optimally processing the accelerometer signal for detection of phrenic nerve activation involves at least filtering to attenuate frequencies less than about 5 Hz.

In some cases, additional filtering may further enhance the signal for phrenic nerve activation detection. For example, heart sounds can modulate the accelerometer signal and may interfere with phrenic nerve activation detection. In some embodiments, one or more notch filters may be used to attenuate noise frequencies in the sensor signal. For example, a notch filter which is adaptive based on cardiac rate may be used to attenuate the band of frequencies associated with heart sounds in the accelerometer signal.

Figure 12:
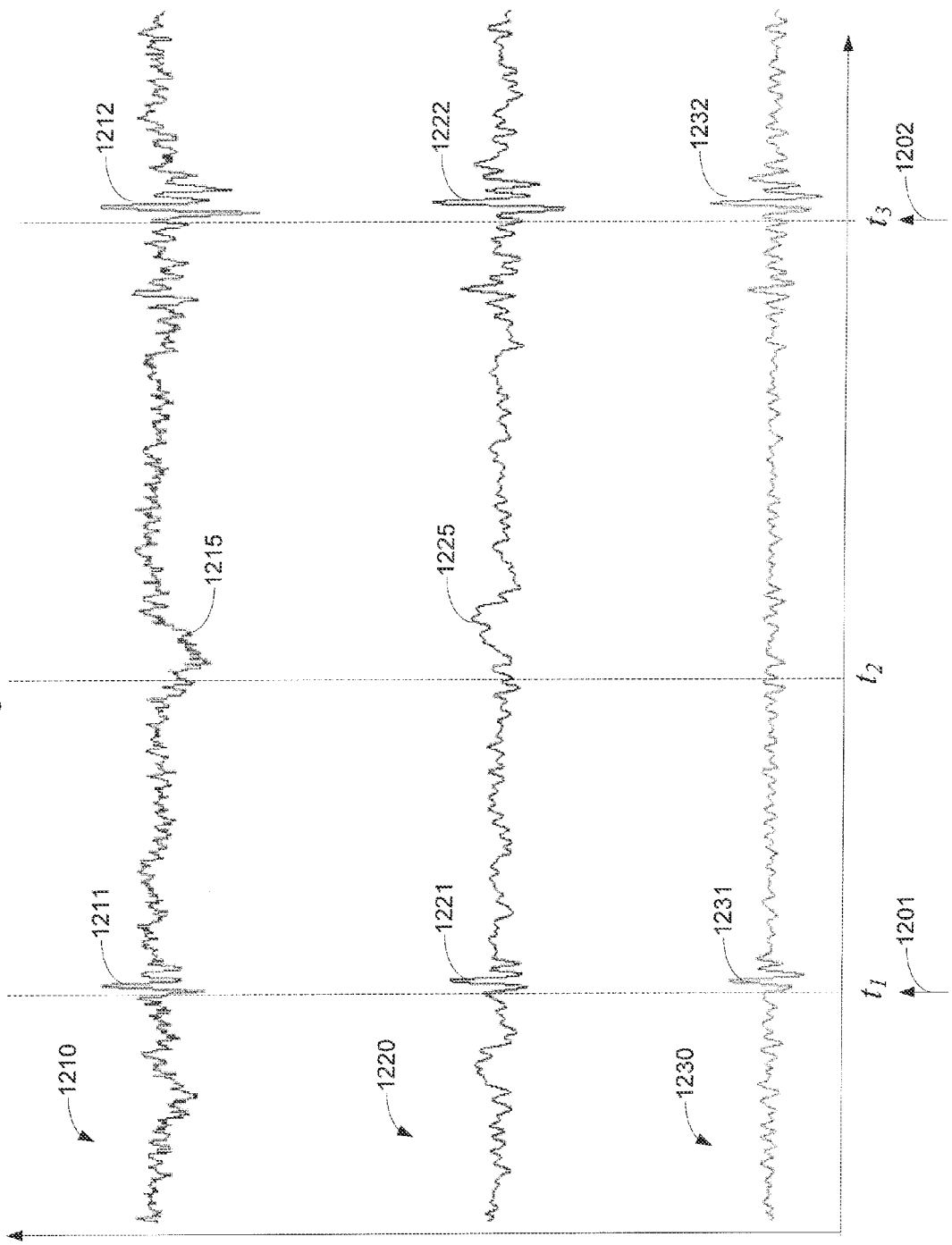
FIG. 12 illustrates the output of an accelerometer before and after processing by two different signal processing circuits.

FIG. 12 illustrates the output of an activity sensor (accelerometer) before and after processing by two different signal processing circuits. Graph 1210 shows the unfiltered accelerometer signal. Graph 1220 shows the accelerometer signal using filter characteristics suitable for activity sensing. Graph 1230 shows the accelerometer signal processed using filter characteristics selected for detection of phrenic nerve activation. At times $t_1$ and $t_3$, phrenic nerve activations 1201, 1202 occur. Graphs 1210 and 1220 show deflections 1211, 1221, 1212, 1222 that are marginally detectable over background noise. At time $t_2$ the patient moves, causing a deflection 1215 in graph 1210 and a deflection 1225 in graph 1220 associated with the patient motion. The deflections 1215 and 1225 in graphs 1210, 1220 caused by patient motion could result in an erroneous phrenic nerve activation detection if the signal 1220 filtered for activity sensing was used.

Graph 1230 illustrates the accelerometer signal processed using filter characteristics selected for optimal detection of phrenic nerve activation. As can be seen in FIG. 12, the phrenic nerve activations 1201, 1202 that occur at times $t_1$ and $t_3$ cause deflections 1231 and 1232 which have a much higher signal to noise ratio than deflections 1211, 1212 in the unfiltered activity signal 1210 or deflections 1221, 1222 in the activity signal. Additionally, the patient movement at time $t_2$ is attenuated and does not cause a deflection in graph 1230, thus avoiding the potential for an erroneous detection of phrenic nerve activation.

Consider an implementation that uses an MV sensor to determine the patient's metabolic demand for adapting the pacing rate. An MV sensor can be implemented by measuring thoracic impedance which is modulated by respiration. Thoracic impedance measurement circuitry includes drive circuitry and impedance measuring circuitry. The drive circuitry supplies a current signal of a specified amplitude, such as one or more constant current pulses, to drive electrodes that are disposed in the patient's thorax. Voltage sense electrodes are disposed at locations within the thorax so that the difference in potential between the voltage sense electrodes during the current pulses is representative of the thoracic impedance between the voltage sense electrodes. Cardiac electrodes, including intracardiac electrodes and/or the conductive housing or can of an implantable pacemaker or defibrillator, can be used as drive electrodes and/or voltage sense electrodes. The impedance measuring circuitry processes the voltage sense signal from the voltage sense electrodes to derive the impedance signal. The impedance signal is modulated by respiration and thus provides the respiration signal as illustrated in FIG. 2. Minute ventilation (MV) is derived from the respiration signal as the amount of air inhaled or exhaled in one minute.

As the patient engages in physical activity, or otherwise experiences an increase in metabolic demand, the depth and/or rate of respiration increases which causes an increase in the measured MV. The value of the MV is used in rate-adaptive pacing to calculate the sensor indicated rate (SIR). The respiration signal from which MV and the SIR are calculated, includes relatively low frequency components. For example, normal breathing at about 12 breaths/minute causes oscillations in the thoracic impedance signal at about 0.2 Hz. In contrast, phrenic nerve activation produces a reflex having frequency components similar to a hiccup reflex, with modulation of the thoracic impedance signal at frequencies that are substantially higher than normal breathing. For example, the inspiratory duration of the phrenic nerve activation may be less than about 150 ms, whereas the inspiratory duration of normal breathing is closer to about 1 to 2 sec.

Figure 13:
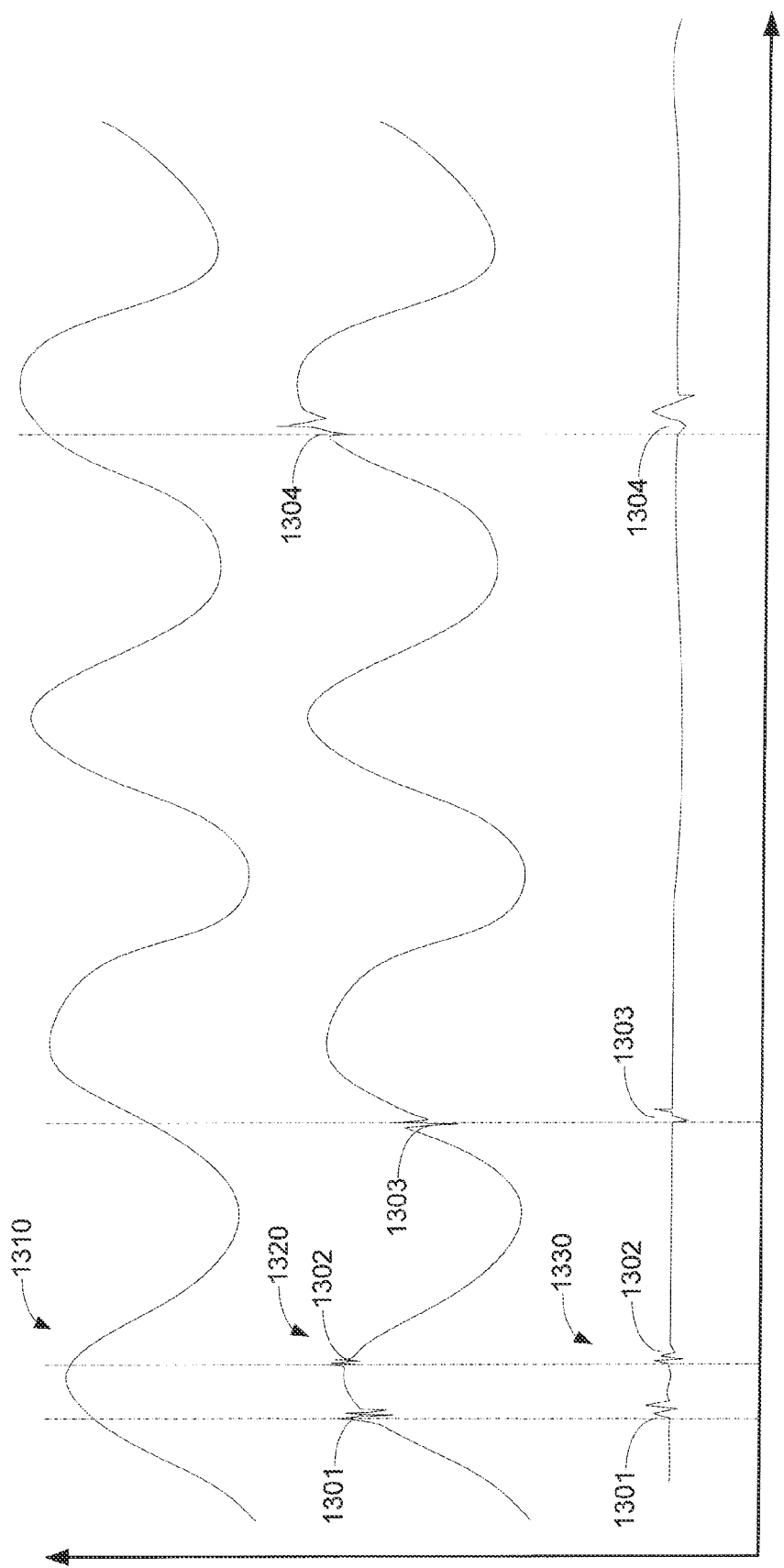
FIG. 13 depicts three graphs representing a thoracic impedance signal that is produced using different three sets of signal processing characteristics.

FIG. 13 depicts three graphs 1310, 1320, 1330 representing the thoracic impedance signal that is produced using different three sets of signal processing characteristics. The first graph 1310 illustrates a respiration signal processed by circuitry that is selected to detect respiration cycles and determine MV. For example, to obtain signal 1310, the output of the thoracic impedance sensor may be digitized using a sampling rate of about 20 Hz and filtered to remove noise including the cardiac component of the signal. In FIG. 1310, the thoracic impedance sensor is filtered using a bandpass filter. The low frequency cut off may be about 0.1 Hz. The high pass cut off frequency of the bandpass filter may be adaptable to substantially attenuate the cardiac component and/or other noise from the sensor signal. The high frequency cut off may be adaptable in a range, e.g., from about 0.5 Hz to up to about 4 Hz. For example, an upper frequency cutoff of about 1.5 Hz may be used to substantially attenuate the cardiac component for heart rates up to about 90 bpm. An upper frequency cutoff of about 4 Hz may be used to substantially attenuate the cardiac component for heart rates up to about 220 bpm. Other high frequency cut offs may be used for other cardiac rates. Processing the thoracic impedance signal using signal processing characteristics suitable for respiration sensing produces a signal that is under-sampled and over-filtered for detecting the altered respiratory state during phrenic nerve activation.

Graph 1320 represents a thoracic impedance signal processed to obtain the higher frequency deflections 1301, 1302, 1303, 1304 in the impedance signal caused by phrenic nerve activations. The signal illustrated in graph 1320 is digitized by sampling at a higher rate than that used for graph 1310, e.g., about 100 Hz, to allow reconstruction of the higher frequencies. The high frequency cutoff of the filtering used to acquire graph 1320 is extended beyond that used to obtain graph 1310, so that the higher frequency phrenic nerve activation components are not substantially attenuated. Additionally, one or more notch filters may be used to attenuate the cardiac component and/or other noise frequencies from the sensor signal. The notch filter may be adaptable based on cardiac rate. In various implementations, the notch filter may attenuate frequencies in the range of about 0.5 to about 4 Hz. For example, notch filtering in the range of about 0.5 Hz to about 1.5 Hz may be used to attenuate the cardiac component for a cardiac rate of about 90 bpm. An upper notch frequency of about 4 Hz may be used to attenuate the cardiac component for a cardiac rate of about 220 bpm.

The signal represented by graph 1320 could be used for both respiration sensing and phrenic nerve activation sensing. However, it can be appreciated that the deflections 1301, 1302, 1303, 1304 caused by phrenic nerve activation superimposed on the respiration signal may be difficult to discern and that additional filtering could enhance the signal for phrenic nerve activation detection.

Using a high pass filter, the respiration and cardiac components of the MV signal can be substantially removed, as illustrated in graph 1330. In one example, filtering for phrenic nerve activation sensing may involve the use of a filter having a low frequency cutoff of about 5 Hz and a high frequency cut off of about 20 Hz. This filtering implementation substantially attenuates low frequency noise, the respiration component, and the cardiac component from the thoracic impedance signal, while retaining frequencies indicative of the phrenic nerve activations 1301, 1302, 1303, 1304.

Returning now to FIG. 11A, the output 1112 of the first signal processing circuitry 1111 may comprise an activity or metabolic demand signal which is optimally filtered for that purpose and is used by rate adaptive pacing control circuitry 1115 to determine a sensor indicated rate (SIR) 1117. The output 1112 of the first signal processing circuitry 1111, e.g., respiration signal or patient activity signal, etc., may also be used to track the parameters sensed directly using the sensor or derived from the sensor signal for diagnostic or other purposes.

The output 1122 from the second signal processing circuitry 1121 is optimally filtered for detection of phrenic nerve activation as described, for example, in connection with FIGS. 12 and 13. The output 1122 is coupled to phrenic nerve activation detection circuitry 1125. The phrenic nerve activation detection circuitry 1125 analyzes the signal 1122 and provides an output 1127 indicating the presence or absence of phrenic nerve activation. The output 1127 from the phrenic nerve activation detection circuitry can be used in conjunction with a cardiac capture threshold test to determine a cardiac pacing threshold or pacing output configuration that avoids phrenic nerve activation.

The filters used in the first signal processing circuitry 1111 and the filters used in the second signal processing circuitry 1121 may be of any suitable type, including any combination of high pass, low pass, band pass, and/or notch filters. In some implementations, for example, a number of filters may be arranged in series. The filters may use various technology implementations including any combination of analog and/or digital filters, e.g., $1^{st}$, $2^{nd}$, or Nth-order filters, non-recursive (finite impulse response (FIR)), recursive (infinite input response (IIR)), Chebyshev, Bessel, Butterworth, etc.

Some embodiments use filter circuitry in the second signal processing circuitry 1121 that is matched to the analog front-end filter circuitry, which may be implemented in the pre-processing circuitry 1109. Since the diaphragmatic "hiccup" caused by phrenic nerve activation resembles an impulse function, the resultant sensor signal 1107 after the analog filtering is applied in the pre-processing circuitry will be close to the impulse response of the pre-processing analog filtering. The filter circuitry in the second signal processing circuitry 1121 may include a filter with characteristics matched to the impulse response of the analog filtering of the pre-processing circuitry 1109. The matched filter would pass phrenic nerve activation signals and substantially reject non-phrenic nerve activation signals, including non-impulse responses along with low frequency noise. In some implementations, the characteristics of the matched filter would be predesignated based on the design of the system. In some implementations, the characteristics of the matched filter could be individually mapped based on an example impulse response during device testing.

Figure 11B:
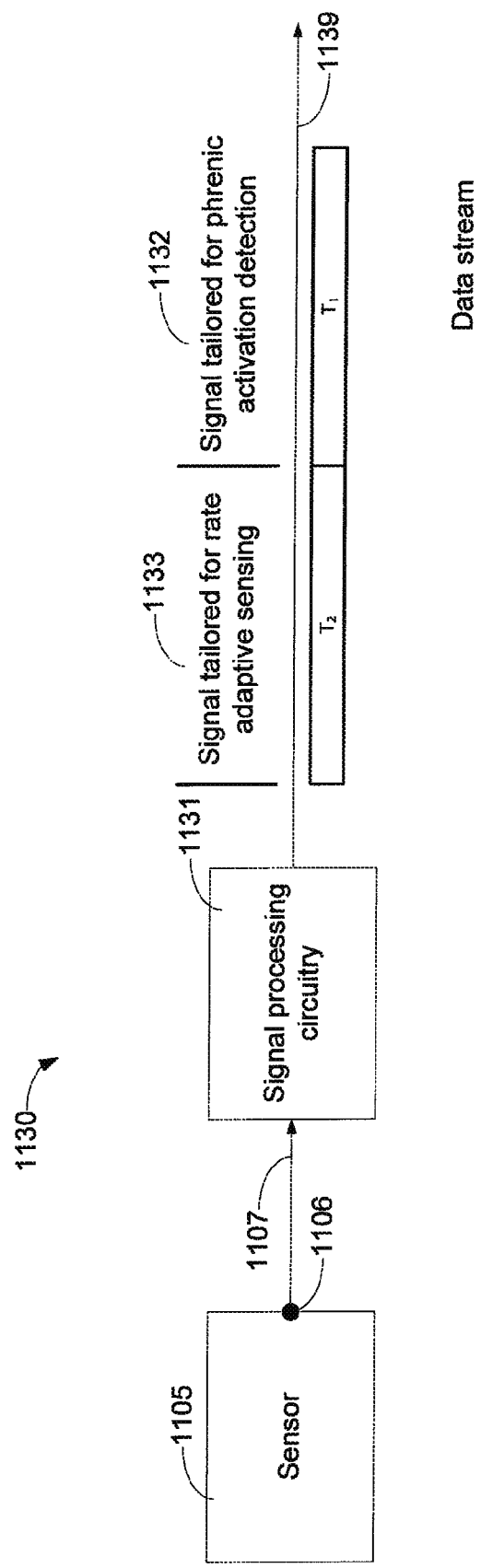
FIG. 11B is a block diagram of medical device circuitry having a single signal processing channel configured to implement time-multiplexed signal processing functions in accordance with embodiments of this disclosure.

In some embodiments, the medical device does not have physically separate channels for processing the sensor signal for detecting the rate adaptation parameter and processing the sensor signal for phrenic nerve activation detection. In these embodiments, as illustrated by FIG. 11B, a single signal processing channel 1130, including signal processing circuitry 1131 is used to implement time-multiplexed signal processing functions. The signal processing circuitry 1131 may include an A/D converter, filters, amplifiers, etc. The single channel 1130 is programmable to apply different signal processing characteristics to the sensor signal 1107 during different time periods. The output 1139 of the signal processing circuitry 1131 is a data stream that includes a first portion of the signal 1132 that is optimal for phrenic nerve activation detection during time interval, $T_1$, and includes a second portion of the signal 1133 that is optimal for activity/metabolic demand sensing for rate-adaptive pacing during a second time period, $T_2$. A first set of signal processing characteristics (A/D conversion characteristics, amplifier characteristics, filter characteristics, etc.) is applied by the signal processing circuitry 1131 to the sensor signal 1107 to produce the portion of the signal 1132 tailored for phrenic nerve activation detection which is output during $T_1$. A second set of signal processing characteristics is applied by the signal processing circuitry 1131 to the sensor signal 1107 to produce the portion of the signal 1133 tailored for activity/metabolic demand sensing for rate-adaptive pacing and/or other functions during $T_2$.

The embodiment of 11B reduces the circuitry required to apply different signal processing characteristics for activity/metabolic demand determination and phrenic nerve activation detection. The phrenic nerve activation detection functionality may be unused other than during a cardiac capture threshold test and/or during periods wherein sensing for phrenic nerve activation is desirable.

The use of both an activity sensor (e.g., accelerometer) and a metabolic demand sensor (e.g., MV sensor) for rate-adaptive pacing has been used to exploit the strengths of both sensor types and achieve a more physiologic adaptation of pacing rate. In some configurations, the outputs of an accelerometer and an MV sensor are blended such that the accelerometer is used during an initial phase of rate adaptation and the MV sensor is used during a second phase of rate adaptation. For example, the accelerometer output alone may be initially used to adapt the pacing rate, with the influence of the accelerometer output decreasing with time as the output of the MV sensor becomes more predominantly used for rate adaptation.

Figure 14A:
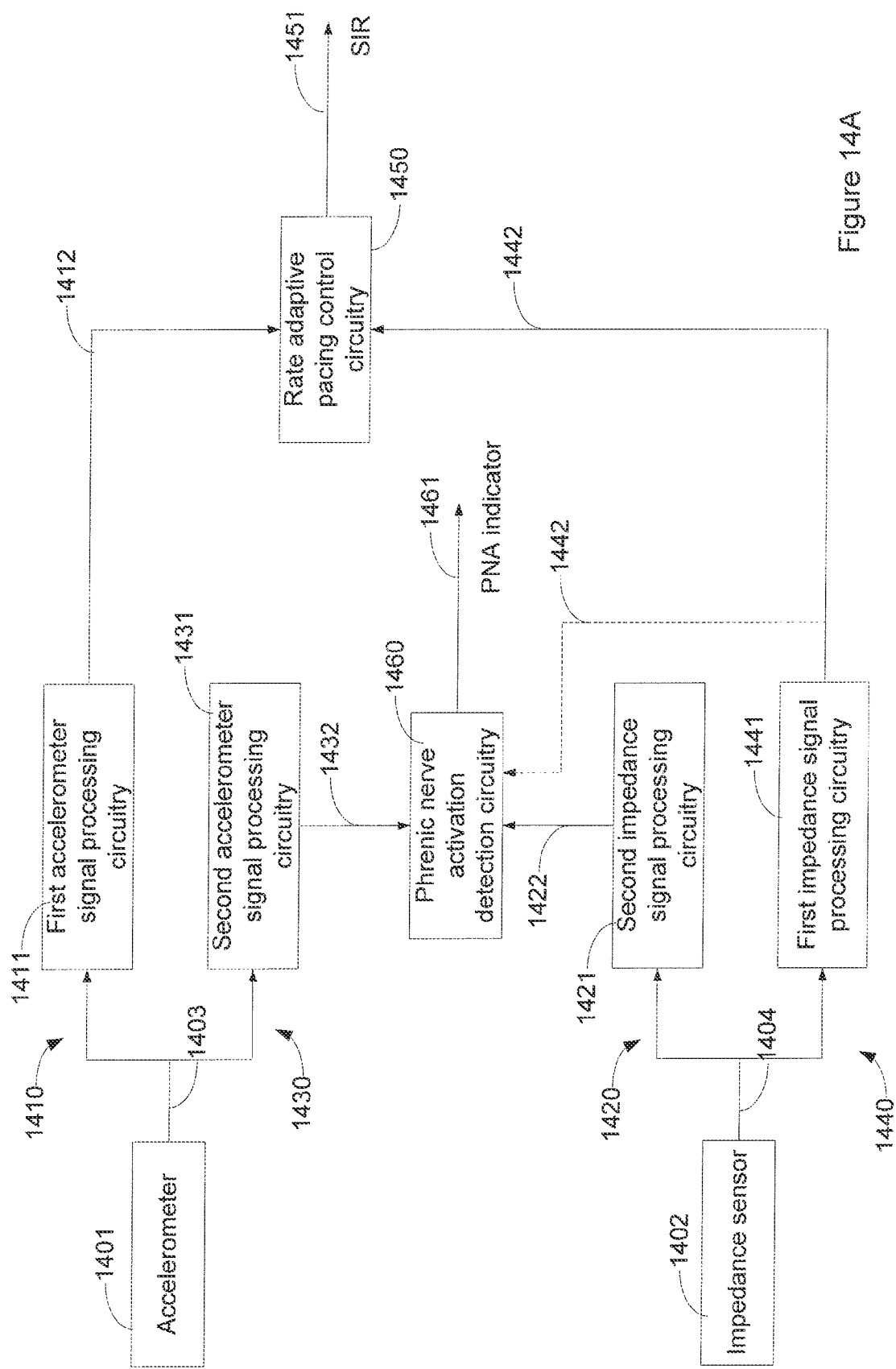
FIGS. 14A-14C are block diagrams of medical devices configured to detect phrenic nerve activation and to use blended sensor outputs for rate adaptation in accordance with embodiments of this disclosure.
Figure 14B:
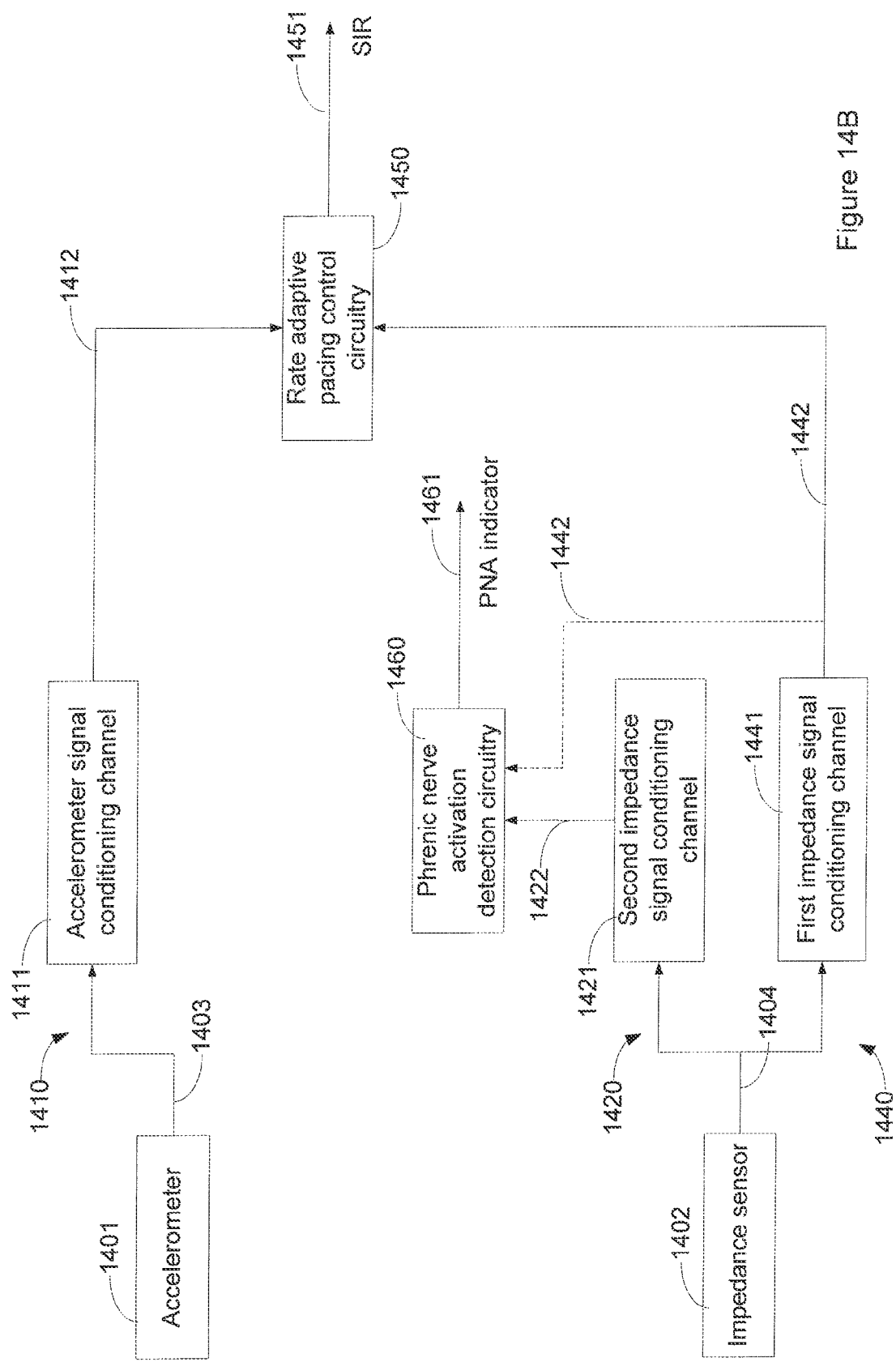
Figure 14C:
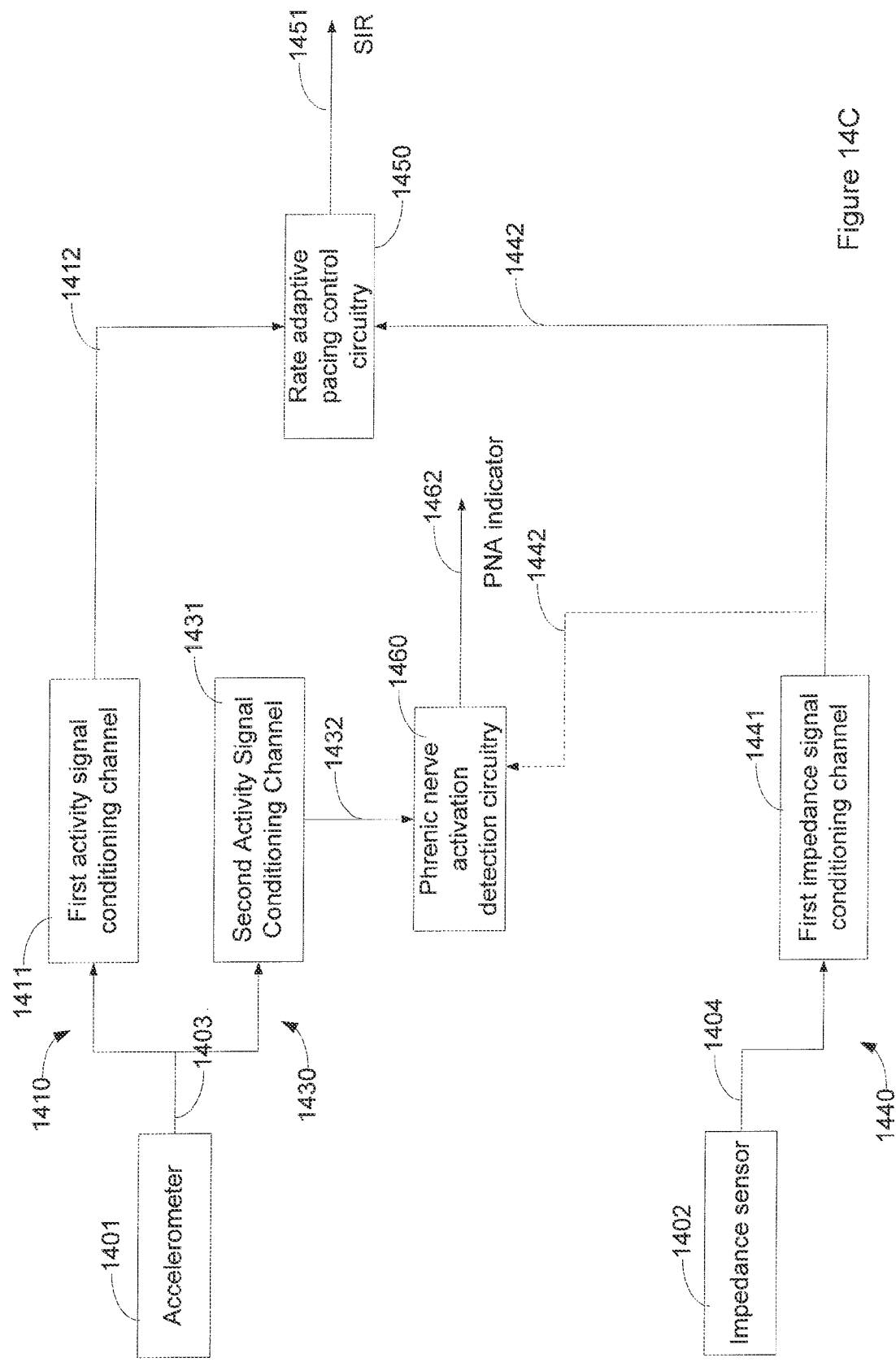

Medical devices that use blended sensor outputs for rate adaptation are illustrated in FIGS. 14A-C. The illustrated devices include an accelerometer 1401 and an MV sensor 1402. The outputs from the accelerometer 1401 and the MV sensor 1402 are processed by first signal conditioning channels 1410, 1440 having circuitry 1411, 1441 designed for activity sensing and respiration sensing, respectively. The output of the first accelerometer signal processing circuitry 1412 and the output of the first impedance signal processing circuitry 1442 are used by rate-adaptive pacing control circuitry 1450 to develop a sensor indicated rate signal 1451.

One or both of the accelerometer signal 1403 and the impedance sensor signal 1404 may additionally be processed using a separate channel 1430, 1420 having circuitry 1431, 1421 designed for enhanced detection of phrenic nerve activation. The signal output(s) 1432, 1422 of the second signal processing circuitry 1431, 1421, are used by the phrenic nerve activation detection circuitry 1460 to detect phrenic nerve activation. Based on one or both signals 1432, 1422, the phrenic nerve activation circuitry 1460 outputs a signal 1461 indicative of phrenic nerve activation (PNA).

FIG. 14C illustrates a medical device that detects phrenic nerve activation based on signal deflections caused by phrenic nerve activation in the signal output 1432 from the second accelerometer signal processing circuitry 1431. FIG. 14B illustrates a medical device that detects phrenic nerve activation based on signal deflections caused by phrenic nerve activation in the signal output 1422 from the second impedance signal processing circuitry 1421.

FIG. 14A illustrates a medical device that detects phrenic nerve activation based on both the output 1432 of the second accelerometer signal processing circuitry 1431 and the output 1422 of the second impedance signal processing circuitry 1421. Using both outputs 1432, 1422 to detect phrenic nerve activation may involve, for example, comparing each output 1432, 1422, respectively, to a threshold and detecting phrenic nerve activation based on the comparison of both signals 1432, 1422 to their respective thresholds. In some implementations, the signal 1432, 1422 derived from one sensor, e.g., accelerometer 1401, thoracic impedance 1402, may be used to initially detect phrenic nerve activation, and the signal 1422, 1432 derived from the other sensor, e.g., thoracic impedance 1402, 1401, accelerometer, may be used to confirm the initial detection of phrenic nerve activation.

As previously discussed above, the threshold for phrenic nerve activation may be lower during certain phases of the respiration cycle making phrenic nerve activation more prevalent during these respiration cycle phases. In these situations, phrenic nerve activation detection may be enhanced by taking into account the phase of the respiration cycle. As indicated in FIGS. 14A-C, the signal output 1442 from the first impedance signal processing circuitry, which is designed for sensing respiration cycles, may be used by the phrenic nerve activation detection circuitry 1460 to detect phrenic nerve activation based on respiration cycle phase.

Figure 15:
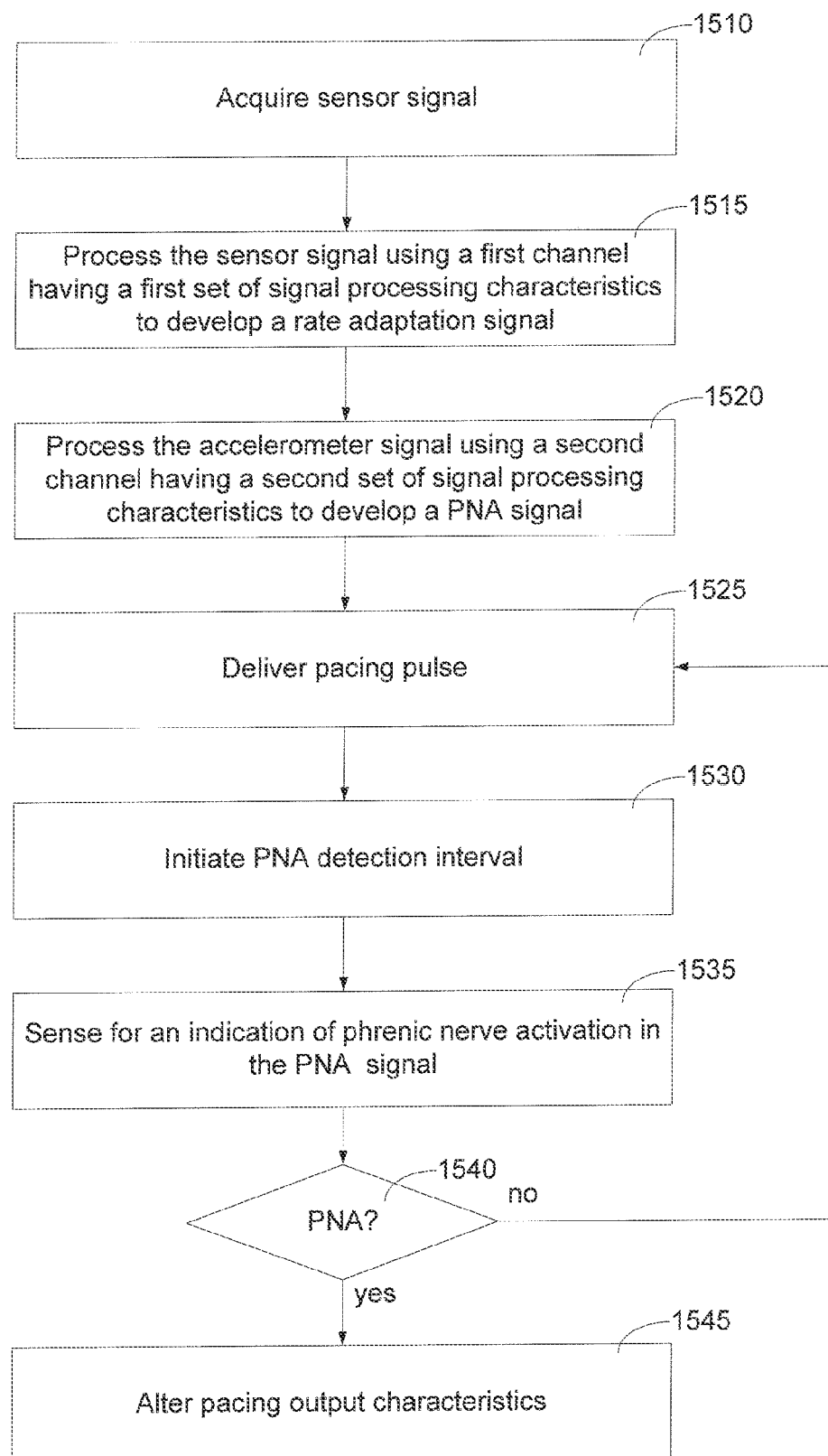
FIG. 15 is a flow diagram illustrating processes implementable in a cardiac device for detecting phrenic nerve activation using a phrenic nerve activation detection interval in accordance with embodiments of this disclosure.

The flow diagram of FIG. 15 illustrates processes implementable in a CRM device for detecting phrenic nerve activation. FIG. 15 illustrates an implementation for PNA detection based on acquiring 1510 a sensor signal which is modulated by a physiological parameter modulated by hemodynamic requirements of the patient, e.g., activity or MV. The sensor signal is processed 1515 using a first channel having a first set of signal processing characteristics to develop a rate-adaptation signal. The sensor signal is processed 1520 using a second channel having a second set of signal processing characteristics to develop a phrenic nerve activation signal. After delivery 1525 of a pacing pulse to a cardiac chamber, a PNA detection interval is initiated 1530. The PNA detection interval may extend for 500 ms, ending before the next pacing pulse to the cardiac chamber is delivered. The device senses 1535 for an indication of PNA in the PNA signal during the PNA detection interval. If PNA is not detected 1540, pacing continues. However, if PNA is detected 1540, the pacing output configuration may be altered 1545 to reduce PNA, or other action may be taken.

The medical devices and processes illustrated in any of FIGS. 11 and 15 can be implemented in the CRM device of FIG. 10 and can be used in conjunction with determination of phrenic nerve activation based on respiration phase, as illustrated, for example, in FIGS. 1-9. The approaches outlined by the flow diagrams of FIGS. 1 and 6 may use the enhanced signal processing for the phrenic nerve activation signal as described herein. These techniques are particularly useful for left ventricular (LV) capture threshold determination since the position of the LV electrodes is more likely to cause phrenic nerve activation.

Although some implementations previously described use an accelerometer signal for phrenic nerve activation detection based on respiration phase, it will be appreciated after reading this disclosure that similar techniques may also be implemented using a phrenic nerve activation signal derived from the thoracic impedance signal. The use of a thoracic impedance sensor for PNA detection may be advantageous in some situations because only one sensor is required to develop the respiration signal, determine a SIR for rate adaptive pacing, and detect phrenic nerve activation based on respiration phase.

Figure 16:
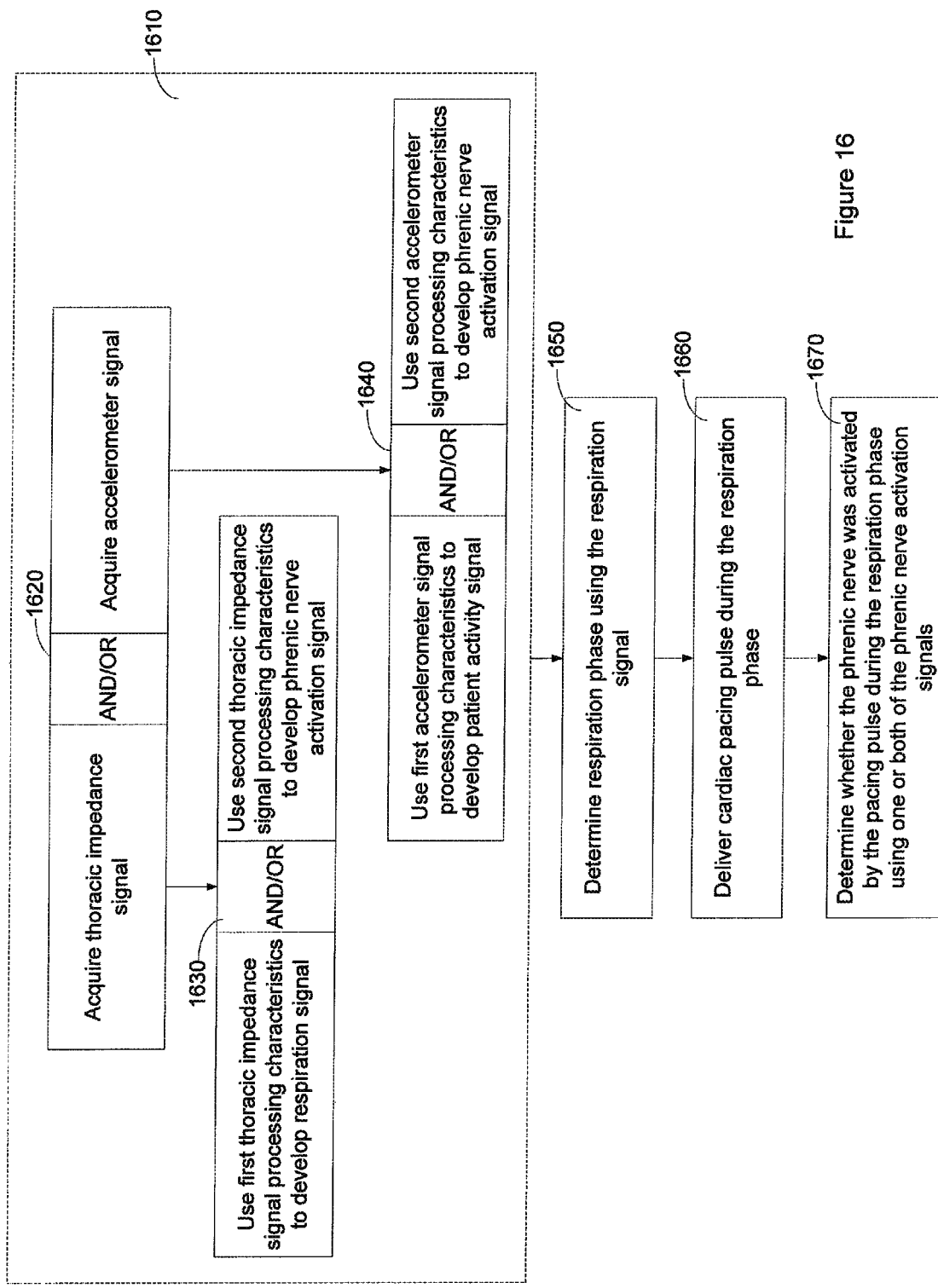
FIG. 16 is a flow diagram illustrating various optional processes for phrenic nerve activation detection in conjunction with respiration rate sensing in accordance with embodiments of this disclosure.

The flow diagram of FIG. 16 illustrates various optional processes that may be used in connection with detection of phrenic nerve activation. In this example, a thoracic impedance signal and/or an accelerometer signal are acquired 1620. The thoracic impedance signal is processed 1630 using first signal processing characteristics to develop a respiration signal. Optionally, the thoracic impedance signal may be processed using second signal processing characteristics to develop a phrenic nerve activation signal. If an accelerometer signal is used, the accelerometer signal may be processed 1640 using first signal processing characteristics to develop a patent activity signal, for example. The accelerometer signal may alternatively or additionally be processed using second signal processing characteristics to develop a phrenic nerve activation signal.

The respiration phase is determined 1650 using the respiration signal, which in this example is developed from the thoracic impedance signal, but in other implementations may be developed using sensors other than a thoracic impedance sensor. A cardiac pacing pulse is delivered 1660 during the respiration phase. The algorithm determines 1670 whether the phrenic nerve was stimulated by the pacing pulse during the respiration phase using one or both of the phrenic nerve activation signal developed from the thoracic impedance signal and the phrenic nerve activation signal developed from the accelerometer.

Figure 17A:
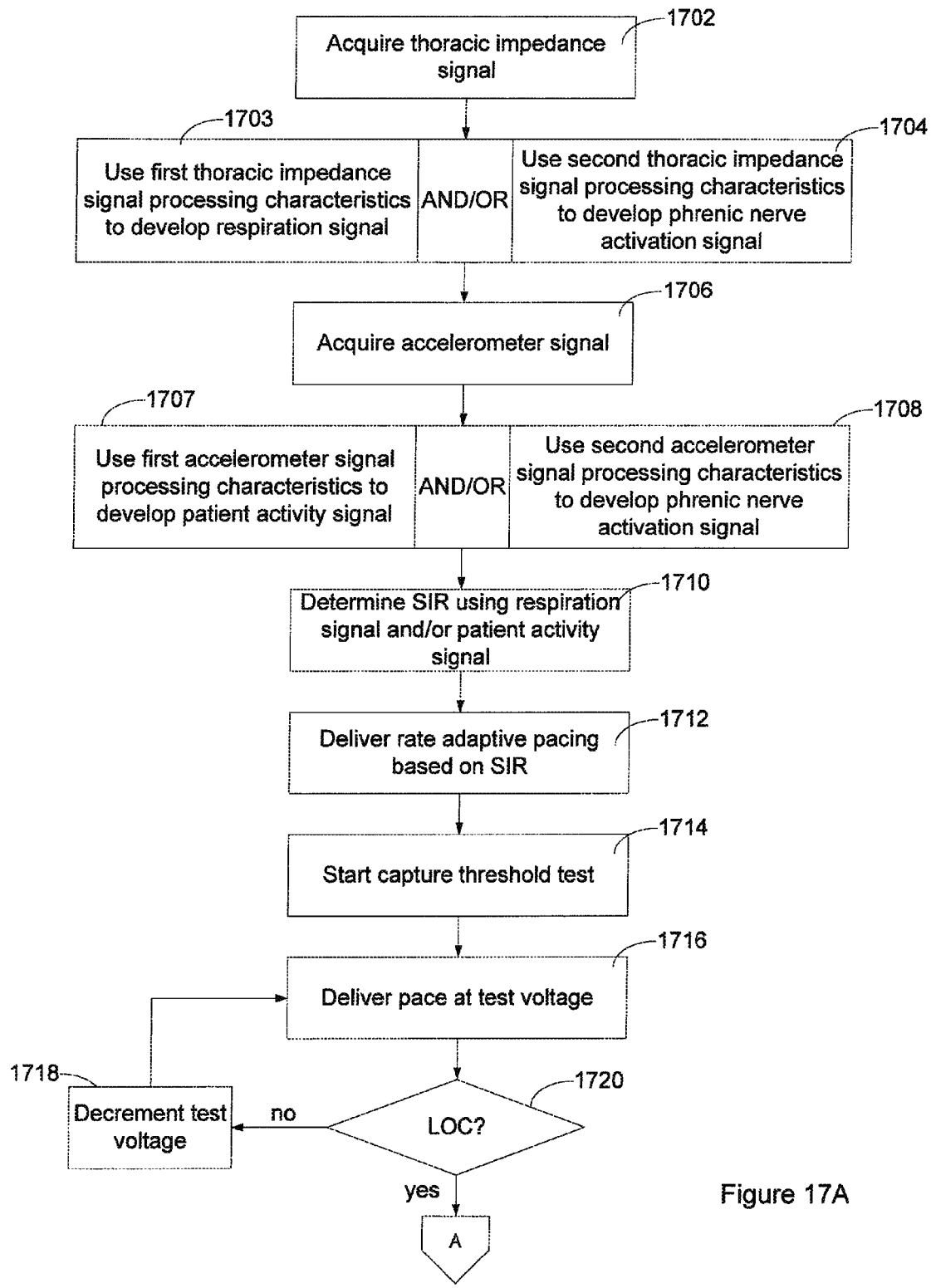
FIGS. 17A-B depict a flow diagram illustrating an algorithm for cardiac capture threshold testing that also includes a process for ensuring that the pacing voltage selected based on the cardiac capture threshold does not produce phrenic nerve activation in accordance with embodiments of this disclosure.
Figure 17B:
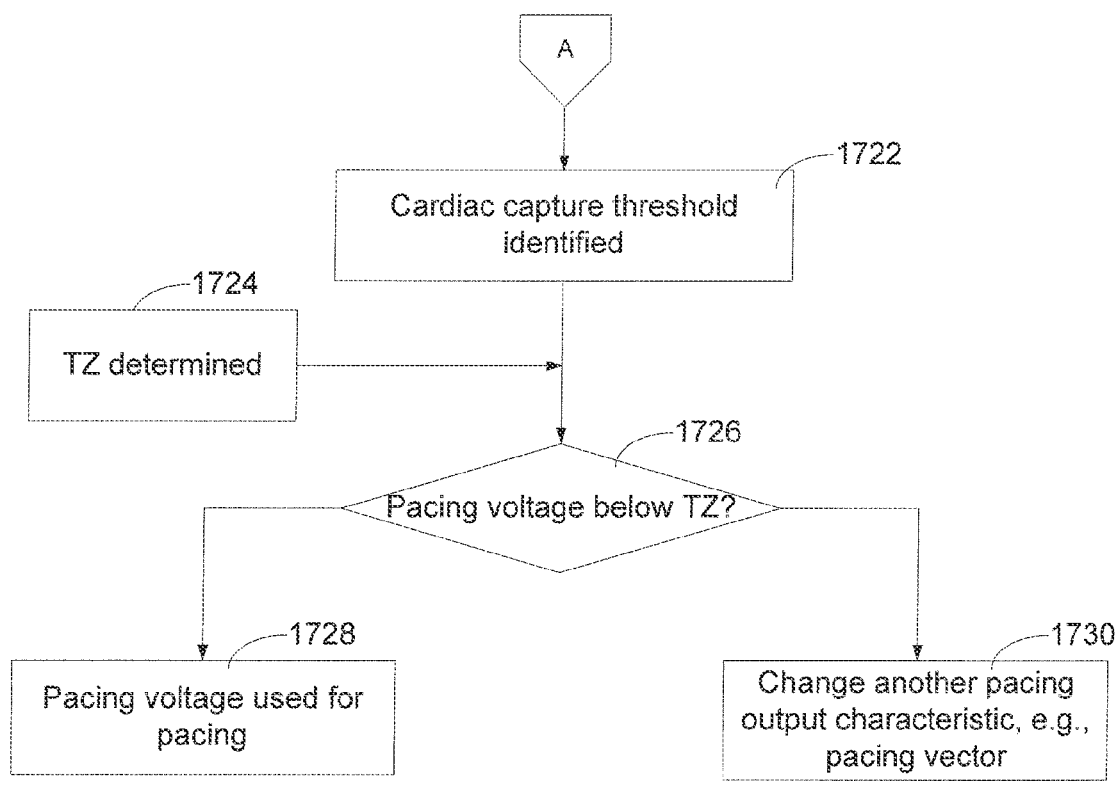

FIGS. 17A-B depict a flow diagram illustrating an algorithm for capture threshold testing that also includes a process for ensuring that the pacing voltage does not produce phrenic nerve activation. The patient's thoracic impedance signal is acquired 1702 by a CRM device. The thoracic impedance signal may be processed using 1703 first thoracic impedance signal processing characteristics to develop the respiration signal. Optionally, the thoracic impedance signal may also be processed using 1704 second thoracic impedance signal processing characteristics to develop a phrenic nerve activation signal.

A signal is acquired 1706 from an accelerometer. The accelerometer signal may be processed using 1707 first accelerometer signal processing characteristics to produce a respiration signal. Alternately or additionally, the accelerometer signal may be processed using 1708 second accelerometer signal processing characteristics to produce a phrenic activation signal.

Normal pacing may involve rate adaptation based on patient activity and/or metabolic need. A sensor indicated rate (SIR) is determined 1710 based on one or both of the respiration signal and the patent activity signal. The SIR is used to adjust 1712 pacing rate based on patient activity and/or metabolic need.

At periodic intervals, on command, or triggered by sensed events, cardiac capture threshold testing is initiated 1714. A cardiac capture threshold test may implement a step-down threshold search, a step-up threshold search, or may use binomial or other search patterns. In the example of FIG. 17A, a step-down search is illustrated. The test pacing voltage is decremented 1718 until loss of capture (LOC) is detected 1720. The pacing voltage just above the test voltage at which LOC is detected is identified 1722 as the cardiac capture threshold for the particular pacing electrode combination under test.

In a process such as the one illustrated in FIG. 7, the transition zone for the electrode configuration is determined 1724. The phrenic nerve activation signal(s) used in determining the transition zone may be one or both of the PNA signal developed using the accelerometer as in block 1708 and the PNA signal developed using the thoracic impedance signal as in block 1704. After the cardiac capture threshold is identified, the algorithm checks 1726 to determine the relationship of the pacing voltage (the cardiac capture threshold plus a safety margin) to the transition zone. In one implementation, if pacing voltage is below the lower boundary of the transition zone, then the pacing voltage is used for pacing. If the pacing voltage is above the lower boundary of the transition zone, then the algorithm may continue searching for an acceptable pacing output configuration by changing a pacing output configuration parameter such as the pulse width or electrode combination, for example. Some implementations may not require that the pacing voltage be below the transition zone boundary and may use the pacing voltage if the pacing voltage falls within a lower portion the transition zone.

The components, functionality, and structural configurations depicted herein are intended to provide an understanding of various features and combination of features that may be incorporated in an implantable pacemaker/defibrillator. It is understood that a wide variety of cardiac monitoring and/or stimulation device configurations are contemplated, ranging from relatively sophisticated to relatively simple designs. As such, particular cardiac device configurations may include particular features as described herein, while other such device configurations may exclude particular features described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

We claim:

1. An implantable medical device, comprising:
   a pulse generator configured to deliver cardiac pacing to a heart;
   an accelerometer configured to generate an acceleration signal at an accelerometer output terminal;
   a first filter channel configured to attenuate first frequencies of the acceleration signal to produce a first physiological signal, wherein the first physiological signal provides a measure of a patient's respiration;
   a second filter channel, separate from the first filter channel, the second filter channel configured to attenuate second frequencies of the acceleration signal to produce a second physiological signal indicative of phrenic nerve activation; and
   circuitry configured to: determine one or more characteristics of a patient's state based at least in part on the first physiological signal, identify a phase of respiration of the patient using the first physiological signal, to detect phrenic nerve activation in a time relation to the phase of respiration caused by cardiac pacing during the phase of respiration based at least in part on the second physiological signal, and to adjust a value of at least parameter of the cardiac pacing based on detected phrenic nerve activation.

2. The device of claim 1, wherein the first filter channel comprises a high frequency cutoff of less than 4 Hz.

3. The device of claim 1, wherein the second filter channel comprises a low frequency cutoff of more than 5 Hz.

4. The device of claim 1, wherein the second filter channel comprises an adaptable notch filter.

5. The device of claim 1, wherein the second filter channel has an adaptable low frequency cutoff.

6. The device of claim 1, wherein one or both of the first filter channel and the second filter channel comprises both analog and digital filters.

7. The device of claim 1, further comprising analog circuitry coupled between the accelerometer output terminal and the first and second filter channels, wherein one or more of the first filter channel and the second filter channel includes a filter circuit that is substantially matched to an impulse response of the analog circuitry.

8. The device of claim 7, wherein the filter circuit substantially attenuates frequencies other than the impulse response frequencies of the analog circuitry.

9. The device of claim 7, wherein the filter circuit is individually mapped to the impulse response during device testing.

10. The device of claim 1, wherein the circuitry includes a timer configured to time a phrenic nerve activation detection interval which is started upon or after delivery of a pacing pulse by the pulse generator to a cardiac chamber and is stopped before delivery of a subsequent pacing pulse to the cardiac chamber.

11. The device of claim 1, wherein the one or more characteristics of the patient's state comprises a patient's activity.

12. The device of claim 1, wherein the one or more characteristics of the patient's state comprises a patient's respiration.

13. The device of claim 1, wherein the first physiological signal is used to provide a measure of a patient's activity level.

14. The device of claim 1, wherein the first physiological signal is used to provide a measure of a patient's metabolic demand.

15. A medical device, comprising:
   a pulse generator configured to deliver cardiac pacing;
   an accelerometer configured to generate an acceleration signal at an accelerometer output terminal;
   circuitry coupled to the accelerometer output terminal, the circuitry configured to have a first set of signal processing characteristics that produce a first physiological signal, the circuitry configured to have a second set of signal processing characteristics that produces a second physiological signal, the first physiological signal indicative of respiration and the second physiological signal indicative of phrenic nerve activation, wherein at least some of the first signal processing characteristics are different from at least some of the second signal processing characteristics; and
   the circuitry configured to: determine one or more characteristics of a patient's state based at least in part on the first physiological signal, identify a phase of respiration of the patient using the first physiological signal, to detect phrenic nerve activation in a time relation to the identified phase of respiration caused by cardiac pacing during the phase of respiration based at least in part on the second physiological signal.

16. The medical device of claim 15, wherein the one or more characteristics of the patient's state comprises one or more of a characteristic related to a patient's activity, a patient's respiration, and a patient's posture.

17. A method of operating an implantable medical device, comprising:
   sensing one or more characteristics of a patient using an accelerometer, and generating a sensor signal at a sensor output terminal of the accelerometer;
   filtering the sensor signal through separate filter channels to produce a first physiological signal and a second physiological signal, the separate filter channels comprising a first filter channel having first filter characteristics configured to attenuate a first set of frequencies from the sensor signal and a second filter channel having second filter characteristics configured to attenuate a second set of frequencies from the sensor signal;

detecting one or more characteristics of respiration using the first physiological signal;

detecting, in a time relation to an identified phase of respiration, phrenic nerve activation caused by cardiac pacing during the identified phase of respiration using the second physiological signal; and producing an output in response to detecting phrenic nerve activation.

18. The method of claim 17, wherein detecting the phrenic nerve activation comprises: sensing for the phrenic nerve activation in the second physiological signal during a phrenic nerve activation detection interval initiated after a cardiac pacing pulse is delivered to a cardiac chamber and terminated before a subsequent cardiac pacing pulse is delivered to the cardiac chamber.

* * * * *